United States Patent
Reisfeld

(10) Patent No.: US 6,301,496 B1
(45) Date of Patent: Oct. 9, 2001

(54) VECTOR MAPPING OF THREE-DIMENSIONALLY RECONSTRUCTED INTRABODY ORGANS AND METHOD OF DISPLAY

(75) Inventor: Daniel Reisfeld, Haifa (IL)

(73) Assignee: Biosense, Inc., New Brunswick, NJ (US)

(*) Notice: Subject to any disclaimer, the term of this patent is extended or adjusted under 35 U.S.C. 154(b) by 0 days.

(21) Appl. No.: 09/357,559

(22) Filed: Jul. 22, 1999

Related U.S. Application Data

(63) Continuation-in-part of application No. 09/122,137, filed on Jul. 24, 1998.

(51) Int. Cl.[7] .................................................... A61B 5/05
(52) U.S. Cl. ......................... 600/407; 600/416; 600/509; 600/515; 600/518; 600/523; 345/419; 345/423; 364/413.06; 382/128
(58) Field of Search .................................... 600/407, 416, 600/509, 515, 518, 523; 345/419, 423; 364/413.06; 382/128

(56) References Cited

U.S. PATENT DOCUMENTS

| | | | |
|---|---|---|---|
| 3,316,896 | 5/1967 | Thomasset | 128/2.1 |
| 4,522,212 | 6/1985 | Gelinas et al. | 128/642 |
| 4,628,937 | 12/1986 | Hess et al. | 128/642 |
| 4,660,571 | 4/1987 | Hess et al. | 128/784 |
| 4,682,603 | 7/1987 | Franz | 128/642 |
| 4,699,147 | 10/1987 | Chilson et al. | 128/642 |
| 4,762,124 | 8/1988 | Kerch et al. | 128/156 |
| 4,898,181 | 2/1990 | Kessler | 128/699 |
| 4,905,705 | 3/1990 | Kizakevich et al. | 128/696 |
| 4,911,174 | 3/1990 | Pederson et al. | 128/695 |
| 4,922,912 | 5/1990 | Watanabe | 128/642 |
| 4,940,064 | 7/1990 | Desai | 128/784 |
| 4,955,382 | 9/1990 | Franz et al. | 128/642 |
| 4,962,767 | 10/1990 | Brownlee | 128/786 |
| 4,979,510 | 12/1990 | Franz et al. | 128/642 |
| 5,022,396 | 6/1991 | Watanabe | 128/642 |
| 5,038,791 | 8/1991 | Collins et al. | 128/696 |
| 5,127,403 | 7/1992 | Brownlee | 128/419 P |
| 5,156,151 | 10/1992 | Imran | 128/642 |
| 5,215,103 | 6/1993 | Desai | 128/784 |

(List continued on next page.)

OTHER PUBLICATIONS

Gerstenfeld E., Sahakian A., Baerman J., Ropella K., Swiryn S. (1991) "Detection of Changes in Atrial Endocardial Activation With Use of An Orthogonal Catheter", JACC. vol. 18, No. 4: 1034–42.

Gerstenfeld E., Sahakian A., Swiryn S. (1992) "Evidence for Transient Linking of Atrial Excitation During Atrial Fibrillation in Humans", Circulation. vol. 86, No. 2: 375–382.

Kadish A., Spear J., Levine J., Hanich R., Prood C., Moore E.N. (1986) "Vector Mapping of Myocardial Activation", Circulation. vol. 74, No. 3: 603–615.

*Primary Examiner*—Marvin M. Lateef
*Assistant Examiner*—Joeyuh Lin
(74) *Attorney, Agent, or Firm*—Frederick L. Herman; Louis J. Capezzuto

(57) ABSTRACT

A method of diagnosing an abnormal condition in a biological structure, such as the heart, including the steps of measuring a physiological response at at least three sampled points on a surface of the biological structure, calculating a vector function related to the response, displaying a representation of the vector function, and inferring the abnormal condition from the representation. The present invention is particularly useful for diagnosing cardiac arrhythmias, in which case the physiological response is a voltage, from which is inferred a local activation time and the vector function is a gradient of the local activation time, specifically, a conduction velocity.

19 Claims, 18 Drawing Sheets

U.S. PATENT DOCUMENTS

| | | | |
|---|---|---|---|
| 5,228,442 | 7/1993 | Imran | 128/642 |
| 5,231,995 | 8/1993 | Desai | 128/784 |
| 5,239,999 | 8/1993 | Imran | 128/642 |
| 5,243,981 | 9/1993 | Hudrlik | 607/11 |
| 5,255,678 | 10/1993 | Deslauriers et al. | 128/642 |
| 5,255,679 | 10/1993 | Imran | 128/642 |
| 5,279,299 | 1/1994 | Imran | 128/642 |
| 5,293,869 | 3/1994 | Edwards et al. | 128/642 |
| 5,297,549 | 3/1994 | Beatty et al. | 128/642 |
| 5,311,866 | 5/1994 | Kagan et al. | 128/642 |
| 5,313,943 | 5/1994 | Houser et al. | 128/642 |
| 5,324,284 | 6/1994 | Imran | 606/15 |
| 5,341,807 | 8/1994 | Nardella | 128/642 |
| 5,345,936 | 9/1994 | Pomeranz et al. | 128/642 |
| 5,377,687 * | 1/1995 | Evans et al. | 128/700 |
| 5,383,917 | 1/1995 | Desai et al. | 607/702 |
| 5,433,198 | 7/1995 | Desai | 128/642 |
| 5,454,370 | 10/1995 | Avitall | 128/642 |
| 5,485,849 | 1/1996 | Panesou et al. | 128/699 |
| 5,487,391 | 1/1996 | Panescu | 128/699 |
| 5,549,109 | 8/1996 | Samson et al. | 128/642 |
| 5,595,183 | 1/1997 | Swanson et al. | 128/697 |
| 5,637,090 | 6/1997 | McGee et al. | 604/95 |
| 5,657,755 | 8/1997 | Desai | 128/642 |
| 5,687,737 * | 11/1997 | Branham et al. | 600/523 |
| 5,697,377 | 12/1997 | Wittkampf | 128/696 |
| 5,718,241 | 2/1998 | Ben-Haim et al. | 128/702 |
| 5,730,704 | 3/1998 | Avitall | 600/374 |
| 5,755,664 | 5/1998 | Rubenstein | 600/377 |
| 5,803,084 * | 9/1998 | Olson | 600/512 |
| 5,842,984 | 12/1998 | Avitall | 600/374 |
| 5,889,524 * | 3/1999 | Sheehan et al. | 345/419 |

\* cited by examiner

VECTOR MAPPING OF THREE-DIMENSIONALLY RECONSTRUCTED INTRABODY ORGANS AND METHOD OF DISPLAY

This is a continuation in part of U.S. patent application Ser. No. 09/122,137 filed Jul. 24, 1998.

FIELD AND BACKGROUND OF THE INVENTION

The present invention relates generally to systems and methods for mapping, and specifically to methods of mapping of intrabody organs.

Cardiac mapping is used to locate aberrant electrical pathways and currents within the heart, as well as mechanical and other aspects of cardiac activity. Various methods and devices have been described for mapping the heart. Such methods and device are described, for example, in U.S. Pat. Nos. 5,471,982, 5,391,199 and 5,718,241 and in PCT patent publications WO94/06349, WO96/05768 and WO97/24981. U.S. Pat. No. 5,391,199, for example, describes a catheter including both electrodes for sensing cardiac electrical activity and miniature coils for determining the position of the catheter relative to an externally-applied magnetic field. Using this catheter a cardiologist may collect a set of sampled points within a short period of time, by determining the electrical activity at a plurality of locations and determining the spatial coordinates of the locations.

In order to allow the surgeon to appreciate the determined data, a map, preferably a three dimensional (3D) map, including the sampled points is produced. U.S. Pat. No. 5,391,199 suggests superimposing the map on an image of the heart. The positions of the locations are determined with respect to a frame of reference of the image. However, it is not always desirable to acquire an image, nor is it generally possible to acquire an image in which the positions of the locations can be found with sufficient accuracy.

Various methods are known in the art for reconstructing a 3D map of a cavity or volume using the known position coordinates of a plurality of locations on the surface of the cavity or volume. Some methods include triangulation, in which the map is formed of a plurality of triangles which connect the sampled points. In some cases a convex hull or an alpha-hull of the points is constructed to form the mesh, and thereafter the constructed mesh is shrunk down to fit on the sampled points within the hull. Triangulation methods do not provide a smooth surface and therefore require additional stages of smoothing.

Another method which has been suggested is forming a bounding ellipsoid which encloses the sampled points. The sampled points are projected onto the ellipsoid, and the projected points are connected by a triangulation method. The triangles are thereafter moved with the sampled points back to their original locations, forming a crude piecewise linear approximation of the sampled surface. However, this method may reconstruct only surfaces which have a star shape, i.e., a straight line connecting a center of the reconstructed mesh to any point on the surface does not intersect the surface. In most cases heart chambers do not have a star shape.

In addition, reconstruction methods known in the art require a relatively large number of sampled locations to achieve a suitable reconstructed map. These methods were developed, for example, to work with CT and MRI imaging systems which provide large numbers of points, and therefore generally work properly only on large numbers of points. In contrast, determining the data at the locations using an invasive catheter is a time-consuming process which should be kept as short as possible, especially when dealing with a human heart. Therefore, reconstruction methods which require a large number of determined locations are not suitable.

One important example of cardiac mapping is the determination of the speed and direction of propagation of electrical signals through the tissue of the heart. Abnormal propagation velocity, or vortical signal flow, may be diagnostic of locally diseased heart tissue that should be treated, for example by ablation. Typically, the velocity of propagation of cardiac signals is measured by sensing the wavefronts at a plurality of electrodes in contact with the inner surface of a chamber of the heart. A representative example of the prior art in this field is Kadish, et al., "Vector Mapping of Myocardial Activation", Circulation, Vol. 74, No. 3, Pages 603–615 (September 1986), in which vectors based on activation maps are drawn perpendicular to the isochrome tangent. Kadish et al. describes the measurement of the timing of local depolarization events, using an array of electrodes, for the purpose of deriving propagation velocities. This propagation velocity deriving technique is also described in Gerstenfeld et al., "Evidence for Transient Linking of Atrial Excitation During Atrial Fibrillation in Humans", Circulation, Vol. 86, No. 2, Pages 375–382 (August 1992) and Gerstenfeld et al., "Detection of Changes in Atrial Endocardial Activation with Use of an Orthogonal Catheter", J. Am. Coll. Cardiol. 1991; 18:1034–42 as well as U.S. Pat. No. 5,487,391 (Panescu).

SUMMARY OF THE INVENTION

It is an object of the present invention to provide an improved method for mapping a 3D volume or cavity, based on the positions of points on a surface of the volume or cavity.

It is an object of some aspects of the present invention to provide methods and apparatus for generating a map of a volume in the human body from a plurality of sampled points, regardless of the shape of the volume.

It is another object of some aspects of the present invention to provide a simple, rapid method for reconstructing a 3D map of a volume in the human body from a plurality of sampled points, preferably using fewer sampled points than is feasible using methods known the art.

It is another object of preferred embodiments of the present invention to provide a method for reconstructing a 3D map of a volume in the human body from a plurality of sampled points, without assuming any topological relationship between the points.

It is another object of some aspects of the present invention to provide a simple method for reconstructing a 3D map of a volume in movement.

It is another object of some aspects of the present invention to provide a simple method for reconstructing a 3D map of a volume in the human body from a plurality of sampled points independent of the sampling order.

It is another object of some aspects of the present invention to provide a quick method for reconstructing a 3D map of a volume in the human body from a plurality of sampled points, such that the method may be used in interactive procedures.

It is another object of some aspects of the present invention to provide a method for reconstructing a smooth 3D map of a volume in the human body from a plurality of sampled points.

In preferred embodiments of the present invention, a processor reconstructs a 3D map of a volume or cavity in a patient's body (hereinafter referred to as the volume), from a plurality of sampled points on the volume whose position coordinates have been determined. In contrast to prior art reconstruction methods in which a large number of sampled points are used, the preferred embodiments of the present invention are directed to reconstruction of a surface based on a limited number of sampled points. The number of sampled points is generally less than 200 points and may be less than 50 points. Preferably, ten to twenty sampled points are sufficient in order to perform a preliminary reconstruction of the surface to a satisfactory quality.

An initial, generally arbitrary, closed 3D curved surface (also referred to herein for brevity as a curve) is defined in a reconstruction space in the volume of the sampled points. The closed curve is roughly adjusted to a shape which resembles a reconstruction of the sampled points. Thereafter, a flexible matching stage is preferably repeatedly performed once or more to bring the closed curve to accurately resemble the shape of the actual volume being reconstructed. Preferably, the 3D surface is rendered to a video display or other screen for viewing by a physician or other user of the map.

In preferred embodiments of the present invention, the initial closed curved surface encompasses substantially all the sampled points or is interior to substantially all the sampled points. However, it is noted that any curve in the vicinity of the sampled points is suitable. Preferably, the closed 3D curved surface comprises an ellipsoid, or any other simple closed curve. Alternatively, a non-closed curve may be used, for example, when it is desired to reconstruct a single wall rather than the entire volume.

A grid of a desired density is defined on the curve, and adjustment of the curve is performed by adjusting the grid points. The grid preferably divides the curved surface into quadrilaterals or any other polygons such that the grid evenly defines points on the curve. Preferably, the grid density is sufficient such that there are generally more grid points than sampled points in any arbitrary vicinity. Further preferably, the grid density is adjustable according to a desired compromise between reconstruction accuracy and speed.

In some preferred embodiments of the present invention, external information is used to choose an initial closed curve which is more closely related to the reconstructed volume, for example, using the image of the volume, as described above. Thus, the reconstruction procedure may produce a more accurate reconstruction in less time. Alternatively or additionally, a database of closed curves suitable for various volumes of the body is stored in a memory, and the curve to be used is chosen according to the specific procedure. In a further preferred embodiment of the present invention, a map of a reconstructed volume in a patient is used as a beginning curve for subsequent mapping procedures performed at later times on the same volume.

Preferably, the rough adjustment of the closed curve is performed in a single iteration, most preferably by calculating for each grid point an adjustment point, and moving the grid point a fraction of the distance to the adjustment point. Preferably, the grid point is moved about 50–80% of the distance between its original point and the adjustment point, more preferably about 75%.

The adjustment point is preferably determined by taking a weighted sum over substantially all the sampled points. Preferably, the weights are inversely related to the distances from the adjusted grid point to the sampled points, referred to herein as grid distances. In a preferred embodiment of the present invention, each weight is defined as the reciprocal of the sum of a small constant plus the grid distance, raised to a predetermined power, so that sampled points close to the grid point are given a larger weight. Preferably, the power is approximately between 4 to 9, most preferably 8. The small constant is preferably smaller than the magnitude of the smallest grid distance, and is preferably of the size of the accuracy of the determination of the coordinates of the sampled points. The small constant is used to prevent division by zero when a grid-point is on a sampled point.

In some preferred embodiments of the present invention, the weights also include a factor which is indicative of the density of points in the vicinity of their corresponding point. Preferably, the weight is multiplied by a density value between zero and one, indicative of the density, such that isolated sampled points influence the sum more than sampled points in a dense area. Preferably, the influence of the points is thus substantially independent of the density of points in their vicinity.

In a preferred embodiment of the present invention, the flexible matching step is performed by associating each sampled point with a corresponding grid-point, such that each sampled point is associated with the grid point which is closest to it. A movement vector is calculated for each of the associated and non-associated grid-points. Preferably, the movement vectors are calculated based on vectors from the associated grid points to their respective sampled points. Further preferably, the sampled points influence the value of the movement vector for a specific point according to their proximity to the specific point. In addition, the function by which the movement vectors are calculated is preferably smooth and does not include complicated calculations. Preferably, the function is a weighted sum of the vectors from the associated grid points to their respective sampled points. The grid points are then moved according to their respective movement vectors.

Additionally or alternatively, the associated grid points are moved toward their corresponding sampled points by a percentage of the distance between them. Those grid points which are not associated with a sampled point are moved a distance which is determined by interpolation between the distances which surrounding points on the grid are moved. Preferably, the resulting grid is smoothed using a suitable smoothing transformation. Preferably, the process of associating and moving is repeated two or more times to allow finer adjustment of the closed curve.

In a preferred embodiment of the present invention, a user can adjust the number of times the flexible matching step is repeated according to a desired compromise between image quality and speed. Alternatively or additionally, a quick reconstruction is first provided to the user, and thereafter the calculation is repeated to receive a finer reconstruction. Preferably, the weights of the weighted sum used in the flexible matching stage are adjusted according to the number of times the matching is to be performed. Alternatively or additionally, the weights are determined for each flexible matching step according to its place in the sequential order of the flexible matching steps.

Preferably, the distances used for the weights and/or for interpolation are Euclidean geometrical distances between the points. The Euclidean distance is easily computed and causes points on opposite walls of the volume to mutually repel, so that the walls do not intersect. Alternatively, other distances, such as the distance along the original or adjusted grid, may be used. In a preferred embodiment of the present invention, during the first flexible matching step the distance used is the distance along the original grid while subsequent flexible matching steps use the Euclidean distance.

In some preferred embodiments of the present invention, a smoothing process is applied to the reconstructed surface, preferably by applying a surface convolution with a Gaussian-like kernel. The smoothing process provides a better approximation of the surface and allows easier performance of calculations based on the reconstructed surface. However, applying the surface convolution results in some shrinkage of the surface, and therefore an affine transformation is preferably performed on the smoothed surface. The affine transformation is preferably chosen according to those sampled points which are external to the reconstructed surface. The chosen affine transformation preferably minimizes the mean square distance of the external points to the surface.

Preferably, when the reconstruction is finished, each sampled point substantially coincides with a grid point. In some preferred embodiments of the present invention, a final exact matching stage is performed. Each sampled point is associated with a closest grid point, and the associated grid point is moved onto the sampled point. The rest of the grid points are preferably not moved. Generally, most of the sampled points are by this stage very close to the reconstructed surface, and therefore the smoothness of the surface is substantially not affected. However, some outlier sampled points, i.e., sampled points which do not belong to the surface, may cause substantial changes to the surface. Preferably, the user may determine whether to move the surface onto points that are distanced from the surface by more than a predetermined maximum distance. Alternatively or additionally, the entire exact matching step is optional and is applied only according to a user request.

Further alternatively or additionally, the grid points are brought to a fixed distance from the sampled points. Leaving such a fixed distance may be desired, for example, when the sampled coordinates are of locations close to a distal tip of a sampling catheter rather than at the distal tip itself.

In preferred embodiments of the present invention, data regarding the sampled points are acquired by positioning a catheter within the volume which is to be reconstructed, for example, within a chamber of the heart. The catheter is positioned with a distal end thereof in contact with each of the sampled points in turn, and the coordinates of the points and, optionally, values of one or more physiological parameters are sensed at a distal end of the catheter. Preferably, the catheter comprises a coordinate sensor close to its distal end, which outputs signals indicative of the coordinates of the tip of the catheter. Preferably, the coordinate sensor determines the position by transmitting and receiving electromagnetic waves, as described, for example, in PCT publications GB93/01736, WO94/04938, WO97/24983 and WO96/05768, or in U.S. Pat. No. 5,391,199, which are all incorporated herein by reference.

In some preferred embodiments of the present invention, the reconstructed volume is in movement, for example, due to beating of the heart. In such embodiments, the sampled points are preferably registered with a reference frame fixed to the heart. Preferably, a reference catheter is fixed in the heart, and the sampled points are determined together with the position of the reference catheter which is used to register the points, as described, for example, in the above-mentioned U.S. Pat. No. 5,391,199 and PCT publication WO96/05768.

Alternatively or additionally, when at least part of the movement is a cyclic movement, as in the heart, acquisition of the sampled points is synchronized to a specific time point of the cycle. Preferably, when the sampled volume is in the heart, an ECG signal is received and is used to synchronize the acquisition of the sampled points. For example, the sampled points may be acquired at end diastole. Further alternatively or additionally, the coordinates of each of the sampled points are determined together with an indication of the time point relative to the cyclic movement in which the coordinates were acquired. Preferably, the indication includes the relative time from the beginning of the cycle and the frequency of the cyclic movement. According to the frequency and the relative time, the determined coordinates are corrected to end diastole, or any other point in the cyclic movement.

In some preferred embodiments of the present invention, for each sampled point a plurality of coordinates are determined at different time points of the cyclic movement. In one of these preferred embodiments, each sampled point has two coordinates which define the range of movement of the point. Preferably, if the plurality of coordinates of different points are associated with different cycle frequencies, the coordinates are transformed so as to correspond to a set of coordinates in a single-frequency cyclic movement. Further preferably, the coordinates are processed so as to reduce or substantially eliminate any contribution due to movement other than the specific (cardiac) cyclic movement, such as movement of the chest due to respiration. Reconstruction is performed for a plurality of configurations of the volume at different time points of the cyclic movement. Preferably, a first reconstruction is performed as described above to form an anchor reconstruction surface, and reconstruction of surfaces for other time points of the cycle are performed relative to the anchor reconstruction surface.

Preferably, for each further time point of the cyclic movement, the anchor surface is adjusted according to the coordinates of the sampled points at the further time point relative to the coordinates of the sampled points of the anchor surface. Preferably, the anchor surface is adjusted by a quadratic transformation which minimizes a mean square error, the error representing the distances between the sampled points of the further time point and the adjusted surface. Alternatively or additionally, an affine transformation is used instead of the quadratic transformation. Further alternatively or additionally, a simple transformation is used for surfaces having relatively few sampled points, while surfaces with a relatively large number of sampled points a quadratic transformation is used. The simple transformation may be an affine transformation, a scaling and rotation transformation, a rotation transformation, or any other suitable transformation.

Preferably, the adjustment of the surface for the further time points includes, after the transformation, one or more, preferably two, flexible matching steps and/or an exact matching stage.

Alternatively or additionally, the reconstruction is performed separately for each of the further time points. Further alternatively or additionally, a first reconstruction of the surfaces for the further time points is performed relative to the anchor surface, and afterwards a more accurate reconstruction is performed for each time point independently.

In some preferred embodiments of the present invention, dedicated graphics hardware which is designed to manipulate polygons is used to perform the reconstruction stages described above.

In some preferred embodiments of the present invention, one or more physiological parameters are acquired at each sampled point. The physiological parameters for the heart may comprise a measure of cardiac electrical activity, for example, and/or may comprise any other type of local information relating to the heart, as described in the above-mentioned PCT patent publication WO97/24981, which is incorporated herein by reference. The one or more physiological parameters may be either scalars or vectors and may comprise, for example, a voltage, temperature, pressure, impedance, conduction velocity, or any other desired value.

It is noted that the physiological response is a time of arrival of a physiological signal propagating in the biological structure and the vector function may be any of a number of vector functions (as noted above). For example, the vector function may be a conduction velocity of the electrical activity.

Preferably, after the volume is reconstructed based on the coordinates, values of the physiological parameter are determined for each of the grid points based on interpolation of the parameter value at surrounding sampled points. Preferably, the interpolation of the physiological parameter is performed in a manner proportional to the aggregate interpolation of the coordinates. Alternatively, the physiological parameters are interpolated according to the geometrical distance between the points on the grid. Alternatively or additionally, the physiological parameters are interpolated in a manner similar to the flexible matching step described hereinabove.

The reconstructed surface may be displayed in movement, and/or a physician may request a display of a specific time point of the cycle. Preferably, the physiological parameter is displayed on the reconstructed surface based on a predefined color scale. In a preferred embodiment of the present invention, the reliability of reconstruction of regions of the reconstructed surface is indicated on the displayed surface. Preferably, regions which are beneath a user-defined threshold are displayed as semi-transparent, using α-blending. Preferably, the reliability at any grid point is determined according to its proximity to sampled points. Those points on the grid which are beyond a predetermined distance from the nearest sampled point are less reliable.

In some preferred embodiments of the present invention, acquired images such as LV-grams and fluoroscopic images are used together with the sampled points to enhance the speed and/or accuracy of the reconstruction. Preferably, the processor performs an object recognition procedure on the image to determine the shape of the closed 3D curved surface to use in constructing the initial grid of the reconstruction. Alternatively or additionally, the image is used by the physician to select areas in which it is most desired to receive sampled points.

In some preferred embodiments of the present invention, the physician may define points, lines, or areas on the grid which must remain fixed and are not to be adjusted. Alternatively or additionally, some points may be acquired as interior points which are not to be on the map since they are not on a surface of the volume. The reconstruction procedure is performed accordingly so that the closed curve is not moved too close to the interior points.

In some preferred embodiments of the present invention, the reconstruction surface is used to determine an accurate estimate of the volume of the cavity. The surface is divided by the grid points into quadrilaterals, and each quadrilateral is further divided into two triangles. Based on these triangles the volume defined by the surface is estimated. Alternatively, the volume is calculated using a volumetric representation. Other measurements, such as geodesic surface measurements on the surface, may also be performed using the reconstructed surface.

It is noted that some of the stages described above may be ignored in some preferred embodiments of the invention, in order to save processing time and speed up the reconstruction procedure.

One example of a physiological parameter to which the present invention is particularly applicable is the local activation time (LAT) of heart tissue. The present invention allows the measurement of LAT, relative to the cardiac cycle, at a plurality of sampled points on the inner surface of a chamber of the heart, using a device, at the tip of a catheter, that senses electrical activity only at a single point of contact of the catheter tip with the inner surface of the chamber of the heart. These measurements of LAT are posted at corresponding points on a grid that corresponds to a particular time in the cardiac cycle, preferably end diastole, and are interpolated to the other grid points. The grid points define polygons, for example, triangles; and a vectorial propagation velocity is determined for each grid polygon from the LAT values at the grid points that are the vertices of the polygon. Each grid then is assigned the average of the propagation velocities of the polygon of which it is a vertex, and the propagation velocities at the grids are smoothed and displayed, preferably as arrows posted at the grid points, with the directions of the arrows representing the direction of propagation and the lengths of the arrows representing the speed of propagation. These arrows provide a visual display of propagation speed and propagation vorticity that enables an electrophysiologist to identify the location of diseased cardiac tissue that should be treated. Note that this measurement and display of propagation velocity is based on consecutive measurements at individual points on the inner surface of the chamber of the heart, unlike the prior art methods, which require simultaneous measurements at at least two distinctly separated points.

More generally, such a display may be constructed for any vector function that is related to a physiological response measured at discrete points on the surface of a biological structure. The vector function may be any of a number of vector functions. For example, the vector function may be a conduction velocity of the physiological response.

LAT is the time interval between a reference time determined, for example, from the body surface ECG or intracardiac electrogram, and the time of the local depolarization event. Other useful scalar functions of the physiological parameters, may be calculated and displayed, superposed on a combined display of LAT (as pseudocolor) and propagation velocity (as arrows). One such useful scalar function is the range of voltages measured at each sampled point (displayed as a pseudocolor): an abnormally low range is diagnostic of scar tissue, upon which the conduction velocity may be displayed as arrows.

There is therefore provided in accordance with a preferred embodiment of the present invention, a method of reconstructing a map of a volume, including determining coordinates of a plurality of locations on a surface of the volume having a configuration, generating a grid of points defining a reconstruction surface in 3D space in proximity to the determined locations, for each of the points on the grid, defining a respective vector, dependent on a displacement between one or more of the points on the grid and one or more of the locations, and adjusting the reconstruction surface by moving substantially each of the points on the grid responsive to the respective vector, so that the reconstruction surface is deformed to resemble the configuration of the surface.

Preferably, the method includes displaying the reconstruction surface.

Preferably, generating the grid includes generating a grid such that the reconstruction surface encompasses substantially all of the determined locations or is interior to substantially all of the determined locations.

Preferably, generating the grid includes defining an ellipsoid.

Preferably, the reconstruction surface is defined and adjusted substantially independently of any assumption regarding a topology of the volume.

Further preferably, the reconstruction surface is defined and adjusted substantially without reference to any point within the volume.

Alternatively or additionally, generating the grid includes acquiring an image of the volume and defining the reconstruction surface such that it resembles the image of the volume.

Further alternatively or additionally, generating the grid includes choosing a grid from a memory library according to at least one characteristic of the volume.

Preferably, adjusting the surface includes a rough adjustment stage and a flexible matching stage.

Preferably, the rough adjustment stage includes moving each point on the grid toward a respective weighted center of mass of the determined locations, and locations closer to the point on the grid are given larger weight.

Preferably, moving each point in the rough adjustment stage includes defining, for each of the points on the grid, a respective rough adjustment vector which includes a weighted sum of vectors from the point to each of the determined locations and moving the points a distance proportional to the respective vector.

Preferably, defining the rough adjustment vector includes calculating a weight for each of the summed vectors that is generally inversely proportional to a magnitude of the summed vector raised to a predetermined power.

Preferably, the weight includes an inverse of a sum of a constant and the magnitude of the vector raised to a power between 4 and 10.

Preferably, the constant is smaller than a precision of the location determination.

Preferably, moving each point includes moving each point toward a respective target point by a distance between 50 and 90% of the distance between the point and the target point.

Preferably, the flexible matching stage includes selecting a grid point to be associated respectively with each of the determined locations.

Preferably, selecting the grid point includes finding for each determined location a point on the grid that is substantially closest thereto.

Further preferably, the flexible matching stage includes moving the selected grid points toward their respective determined locations.

Preferably, moving the selected grid points includes moving the grid points substantially onto their respective, determined locations.

Preferably, the flexible matching stage includes moving grid points that were not selected by an amount dependent on the movements of surrounding grid points.

Preferably, moving the grid points that were not selected includes moving the grid points by an amount dependent substantially only on the movements of surrounding selected grid points.

Preferably, moving the grid points includes calculating a movement of a grid point that was not selected based on the movements of the surrounding selected grid points and distances from these surrounding grid points.

Preferably, calculating the movement of the grid point includes interpolating between the movements of surrounding grid points.

Preferably, the distances include geometrical distances.

Alternatively or additionally, the distances include a length of the reconstruction surface between the grid points.

Preferably, the flexible matching stage includes defining a displacement function which includes a weighted sum of vectors, each vector connecting a location and its associated point.

Preferably, the flexible matching stage includes moving the grid points according to the displacement function so as to smooth the surface.

Preferably, determining the coordinates includes positioning a catheter tip at the plurality of locations.

Preferably, positioning the catheter tip includes positioning the catheter at a plurality of locations in a chamber of the heart.

Preferably, determining the coordinates includes positioning a catheter tip at the plurality of locations.

Preferably, determining the coordinates includes transmitting and receiving non-ionizing waves.

Preferably, determining the coordinates includes positioning at the plurality of locations a device which generates signals indicative of the position of the device.

Preferably, the device generates signals indicative of the six degrees of position and orientation of the device.

Preferably, determining the coordinates includes receiving the coordinates from an external source.

Preferably, the method includes acquiring a signal indicative of a value of physiological activity at substantially each of the plurality of locations.

Preferably, acquiring the signal includes acquiring a signal indicative of a value of electrical activity at the location.

Preferably, the method includes estimating a value of the physiological activity at the adjusted grid points.

Preferably, estimating the value of the physiological activity includes estimating based on an acquired value of the physiological activity at a location in a vicinity of the adjusted grid points.

Preferably, estimating based on the acquired value includes interpolating the value responsive to deformation of the reconstruction surface.

Preferably, determining coordinates of a plurality of locations includes determining coordinates of less than 200 locations, more preferably of less than 50 locations, and most preferably of less than 20 locations.

Preferably, the volume is in motion, and determining the coordinates includes determining a correction factor responsive to the motion.

Preferably, the motion includes cyclic motion, and determining the correction factor includes determining a factor responsive to a cycle frequency of the motion.

Preferably, determining the factor includes filtering out motion at a frequency substantially different from the cycle frequency.

Preferably, the motion includes cyclic motion, and determining the coordinates includes determining the coordinates at a predetermined phase of the cyclic motion.

Preferably, determining the coordinates at the predetermined phase includes determining the coordinates in a plurality of time points and adjusting the coordinates relative to the cyclic movement.

Preferably, adjusting the coordinates includes determining a rate of the cyclic movement together with the coordinates for substantially each coordinate determination.

Preferably, generating the grid and adjusting the reconstruction surface are performed separately with respect to the coordinates determined in each phase of the cyclic motion.

Alternatively or additionally, generating and adjusting are performed for the coordinates of a plurality of phases of the cyclic motion so as to form a motion map of the volume.

Preferably, generating the grid and adjusting the reconstruction surface are performed for a first group of coordinates determined in a first phase of the cyclic motion, and the reconstructed surface of the first group is adjusted to form a reconstructed surface in one or more additional phases.

Preferably, the method includes smoothing the reconstructed surface.

Preferably, the method includes applying an affine transformation to the reconstructed surface.

Preferably, the method includes a final stage in which each determined location is associated with a respective grid point, and the associated grid points are moved onto the determined locations while non-associated grid points are substantially not moved.

Preferably, the method includes estimating a measure of the volume responsive to the reconstructed surface.

Preferably, estimating the measure of the volume includes choosing an arbitrary point inside the grid and calculating the volumes of tetrahedrons defined by the arbitrary point and groups of three points on the grid which cover the entire grid surface.

There is further provided in accordance with a preferred embodiment of the present invention, apparatus for reconstructing a map of a volume from coordinates of a plurality of determined locations on a surface of the volume having a configuration, including a processor, which receives the coordinates and generates a grid of points defining a reconstruction surface in 3D space in proximity to the determined locations, and which defines a respective vector for each of the points on the grid, dependent on a displacement between one or more of the points on the grid and one or more of the locations, and which adjusts the reconstruction surface by moving each of the points on the grid responsive to the respective vector, so that the reconstruction surface is deformed to resemble the configuration of the surface of the volume.

Preferably, the apparatus includes a display screen for displaying the adjusted surface.

Preferably, the processor analyzes the adjusted surface to determine a characteristic of the volume.

Preferably, the apparatus includes a memory for storing the adjusted surface.

Preferably, the grid initially encompasses substantially all of the determined locations.

Preferably, the apparatus includes an imaging device for acquiring an image of the volume, and the processor defines the grid initially such that it resembles the image of the volume.

Preferably, the apparatus includes a memory library including a plurality of closed curves, and the processor defines the grid initially by choosing a closed curve from the memory library according to at least one characteristic of the volume.

Preferably, the processor generates and defines the reconstruction surface substantially independently of any assumption regarding a topology of the volume.

Preferably, the processor generates and defines the reconstruction surface substantially without reference to any point within the volume.

Preferably, the processor forms the adjusted grid in two stages: a rough adjustment stage and a flexible matching stage.

Preferably, in the rough adjustment stage, the processor moves each point on the grid toward a respective weighted center of mass of the determined locations, and locations closer to the point on the grid are given larger weight.

Preferably, the processor calculates the center of mass using a weight that is substantially proportional for each location to the inverse of the sum of a small constant and the distance between the point and the location raised to a power between 4 and 10.

Preferably, the constant is smaller than a precision of the location determination.

Preferably, in the flexible matching stage, the processor selects a respective grid point to associate with each of the determined locations.

Preferably, the selected grid point for each determined location includes a point on the grid that is closest to the location.

Preferably, in the flexible matching stage, the processor moves the selected grid points toward their respective, associated locations.

Preferably, the processor moves the selected grid points onto the associated locations.

Preferably, the processor moves non-selected grid points by an amount dependent on the movements of surrounding grid points.

Preferably, the amount of movement of the non-selected grid points is dependent on the movements of surrounding selected grid points.

Preferably, the amount of movement of each of non-selected grid points is calculated by the processor based on the distances from the surrounding selected grid points to the non-selected grid point.

Preferably, the amount of movement of the non-associated grid points is calculated by the processor based on an interpolation of the movements of surrounding selected grid points.

Preferably, the distances include geometrical distances.

Preferably, the apparatus includes a probe, which is brought into engagement with the surface to determine the locations thereon.

Further preferably, the probe includes a position sensor which indicates the position of a tip of the probe.

Preferably, the sensor includes at least one coil.

Preferably, the sensor generates signals indicative of position and orientation of the sensor.

Alternatively or additionally, the probe includes a functional portion for acquiring a value of a physiological activity at the plurality of locations.

Preferably, the functional portion includes an electrode.

Preferably, the processor estimates a value of the physiological activity at the adjusted grid points.

Preferably, the processor estimates the value of the physiological activity based on the acquired values of the physiological activity at points surrounding the adjusted grid points.

Preferably, the processor estimates the value by interpolation from the acquired values responsive to deformation of the reconstruction surface.

Preferably, the apparatus includes a reference catheter for registering the determined locations relative to a frame of reference associated with the volume.

Preferably, the apparatus includes an ECG monitor for gating the operation of the probe so as to determine the points at a fixed phase of a cyclic movement of the volume.

There is further provided in accordance with a preferred embodiment of the present invention, a method of displaying values of a parameter which varies over a surface, including determining a value of the parameter at each of a plurality of points on the surface, and rendering an image of the surface to a display with a different degree of transparency in different areas of the surface, responsive in each of the areas to the value of the parameter at one or more points in the area.

Preferably, determining the value includes sampling a plurality of points and creating a map of the surface responsive thereto, and rendering the image includes rendering a graphic representation of the map.

Preferably, creating the map includes creating a three-dimensional map.

Preferably, determining the value includes determining a measure of reliability of the map in each of the areas.

Preferably, rendering the image includes rending one or more of the areas having a low measure of reliability relative to another one or more of the areas with a relatively greater degree of transparency.

Preferably, determining the measure of reliability includes determining a density of the sampled points.

Preferably, rendering the image includes defining a color scale and displaying a color associated with the value, at each of the plurality of points.

Preferably, the plurality of points includes sampled points and interpolated points, and determining the measure of reliability includes assigning a high reliability measure to the sampled points.

Preferably, determining the measure of reliability includes assigning measures of reliability to the interpolated points according to their respective distance from a closest sampled point.

There is further provided in accordance with a preferred embodiment of the present invention, a method of diagnosing a condition in a biological structure, including measuring a physiological response at at least three sampled points on a surface of the biological structure, calculating a vector function related to the response, and displaying a representation of the vector function.

Preferably, the vector function is related to a gradient of the physiological response.

Preferably, the physiological response is a function of time.

More preferably, the physiological response is a time of arrival of a physiological signal propagating in the biological structure, and the vector function may be any of a number of vector functions, most preferably it is a conduction velocity.

Preferably, the representation includes an arrow at each sampled point, the length of the arrow being related to the magnitude of the vector function at each sampled point, and the direction of the arrow being related to the direction of the vector function at each sampled point.

Preferably the method further includes fitting a surface to the sampled points and displaying the surface, the display of the representation being superposed on the display of the surface. Here, too, it is preferred that the representation includes an arrow at each sampled point, the length of the arrow being related to the magnitude of the vector function at each sampled point, and the direction of the arrow being related to the direction of the vector function at each sampled point.

Preferably, the fitting of the surface to the sampled points includes representing the surface as a grid that includes at least as many grid points as there are sampled points. More preferably, at least one of the grid points coincides with one of the sampled points.

Preferably, the grid includes a plurality of polygons, with the grid points being the vertices of the polygons, each grid point being a vertex of at least one polygon, and the calculating of the vector function includes the steps of interpolating the response at the grid points, assigning a value of the vector function to each polygon, with the value of the vector function assigned each polygon being based on the interpolated response at the grid points that are the vertices of that polygon, and determining a value of the vector function at each grid point, with the value of the vector function at each grid point being based on the values of the vector function that are assigned to the polygons of which that grid point is a vertex. Most preferably, the polygons are triangles.

More preferably, calculating the vector function further includes smoothing the values of the vector function at the grid points. Most preferably, the smoothing parameters may be determined based on a priori knowledge about the specific heart.

Preferably, the method further includes calculating scalar functions related to the physiological response and displaying representations of these scalar functions superposed on the display of the surface along with the representation of the vector function. An important example of one such scalar function is a range of the physiological response measurements at the sampled points. In another important example, useful in the diagnosis of heart disease, the measurements are voltage measurements, a scalar function is the range of voltage measurements at each sampled point, and the vector function is a conduction velocity inferred from the local activation time.

Preferably, the physiological response is an impedance, wherein the scalar function is a range of the impedances, and the vector function is a conduction velocity.

Preferably, the method further includes inferring the condition from the representation of the vector function. Preferably, inferring the condition includes identifying at least one location on the surface that is afflicted by the condition, and the method further includes the step of treating those locations.

Preferably, the treatment includes ablation of the biological structure at those locations.

Preferably, the physiological response is measured consecutively at the sampled points.

There is further provided, in accordance with a preferred embodiment of the present invention, a method of diagnosing a condition in a biological structure, including measuring a physiological response at at least three sampled points on a surface of the biological structure, calculating a vector function related to the response, and inferring the condition from the vector function.

Preferably, the vector function is related to a gradient of the physiological response.

Preferably, the physiological response is a function of time.

More preferably, the physiological response is a time of arrival of a physiological signal propagating in the biological structure, and the vector function is a velocity of the propagation.

Preferably, inferring the condition includes identifying at least one location on the surface that is afflicted by the condition, and the method further includes the step of treating those locations.

Preferably, the treatment includes ablation of the biological structure at those locations.

Preferably, the physiological response is measured consecutively at the sampled points.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
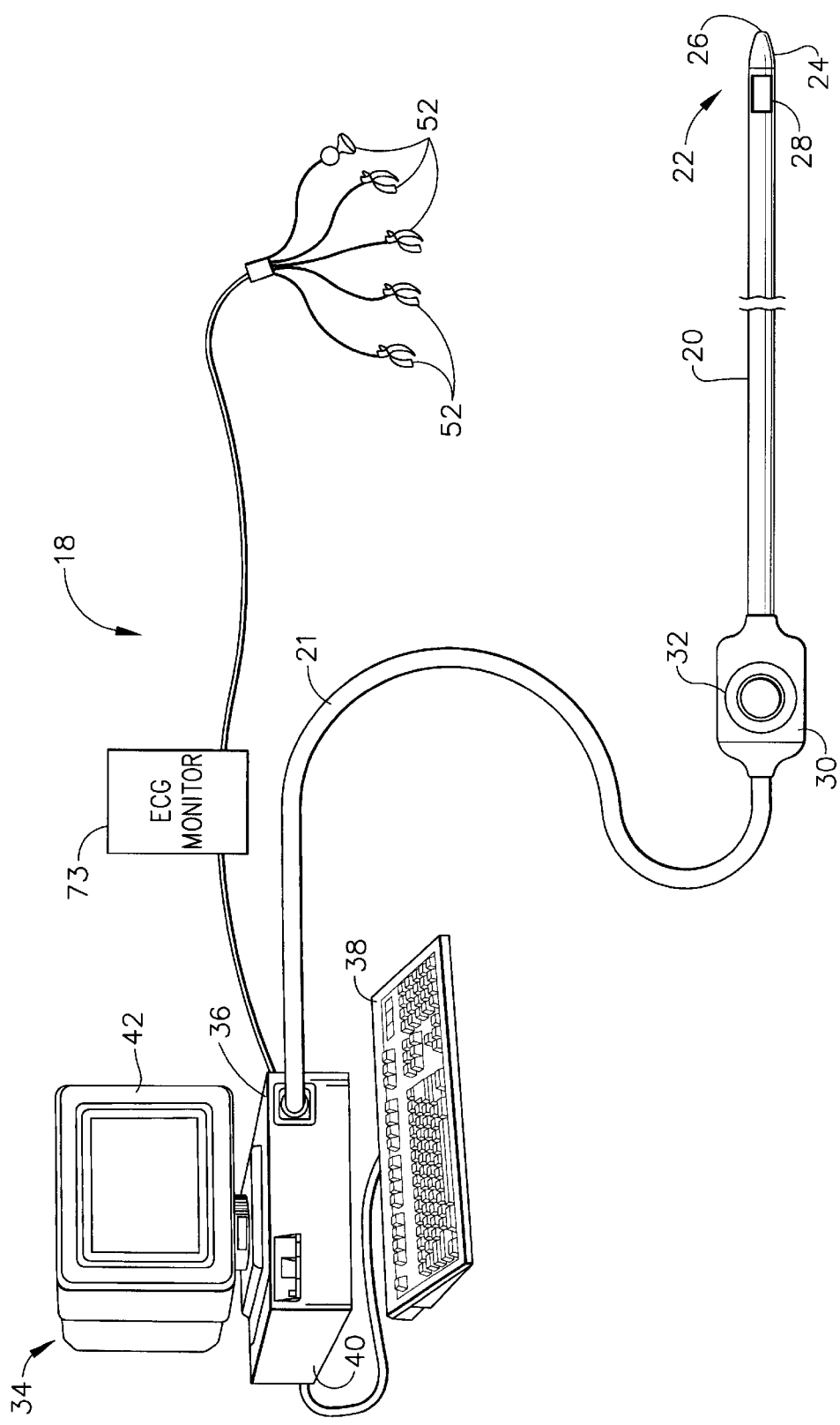
FIG. 1 is a schematic, perspective view of a heart mapping system, in accordance with a preferred embodiment of the present invention.

FIG. 1 shows a mapping system 18 for mapping of a volume in a patient's body, in accordance with a preferred embodiment of the present invention. System 18 comprises an elongate probe, preferably a catheter 20, for insertion into the human body. A distal end 22 of catheter 20 includes a functional portion 24 for performing diagnostic and/or therapeutic functions, adjacent to a distal tip 26. Functional portion 24 preferably comprises electrodes (not shown in the figure) for performing electrophysiological measurements, as described, for example, in U.S. Pat. No. 5,391,199 or in PCT publication WO97/24983, which are incorporated herein by reference. Alternatively or additionally, functional portion 24 may include other diagnostic apparatus for recording parameter values at points within the body. Such apparatus may include a chemical sensor, a temperature sensor, a pressure sensor and/or any other desired sensor. Functional portion 24 may determine for each point a single value of the parameter, or alternatively a plurality of values dependent on the time of their acquisition. Functional portion 24 may also include therapeutic apparatus, as is known in the art.

Distal end 22 of catheter 20 further includes a device 28 that generates signals used to determine the position and, preferably, orientation of the catheter within the body. Device 28 is preferably adjacent to functional portion 24, in a fixed relation with tip 26. Device 28 preferably comprises three non-concentric coils, such as described in PCT patent publication WO96/05768, whose disclosure is incorporated herein by reference. This device enables continuous generation of six dimensions of position and orientation information with respect to an externally-applied magnetic field. Alternatively, device 28 comprises other position and/or coordinate sensors as described in U.S. Pat. No. 5,391,199, U.S. Pat. No. 5,443,489 and PCT publication WO94/04938, which are incorporated herein by reference. Further alternatively or additionally, tip 26 is marked with a marker whose position can be determined from outside of the body, for example, a radio-opaque marker for use with a fluoroscope.

Catheter 20 preferably includes a handle 30, having controls 32 which are used by a surgeon to steer distal end 22 of the catheter in a desired direction, so as to position and/or orient it as desired. Catheter 20 preferably comprises a steering mechanism in distal end 22, as is known in the art, so that repositioning of tip 26 is facilitated.

Catheter 20 is coupled, via an extension cable 21, to a console 34 which enables the user to observe and regulate the functions of catheter 20. Console 34 preferably includes a computer 36, keyboard 38, signal processing circuits 40, which are typically inside the computer, and display 42. Signal processing circuits 40 typically receive, amplify, filter and digitize signals from catheter 20, including signals generated by position signal generating device 28, whereupon these digitized signals are received and used by computer 36 to compute the position and orientation of the catheter. Alternatively, appropriate circuitry may be associated with the catheter itself so that circuits 40 receive signals that are already amplified, filtered and/or digitized. Preferably, computer 36 includes a memory for storing positions and determined parameters of the points. Computer 36 preferably also includes dedicated graphic hardware for polygon manipulation, which allows performing reconstruction stages described hereinbelow using fast computer graphic techniques.

Preferably, system 18 also includes an ECG monitor 73, coupled to receive signals from one or more body surface electrodes 52 and to convey the signals to computer 36. Alternatively, the ECG monitoring function may be performed by circuits 40.

Figure 2:
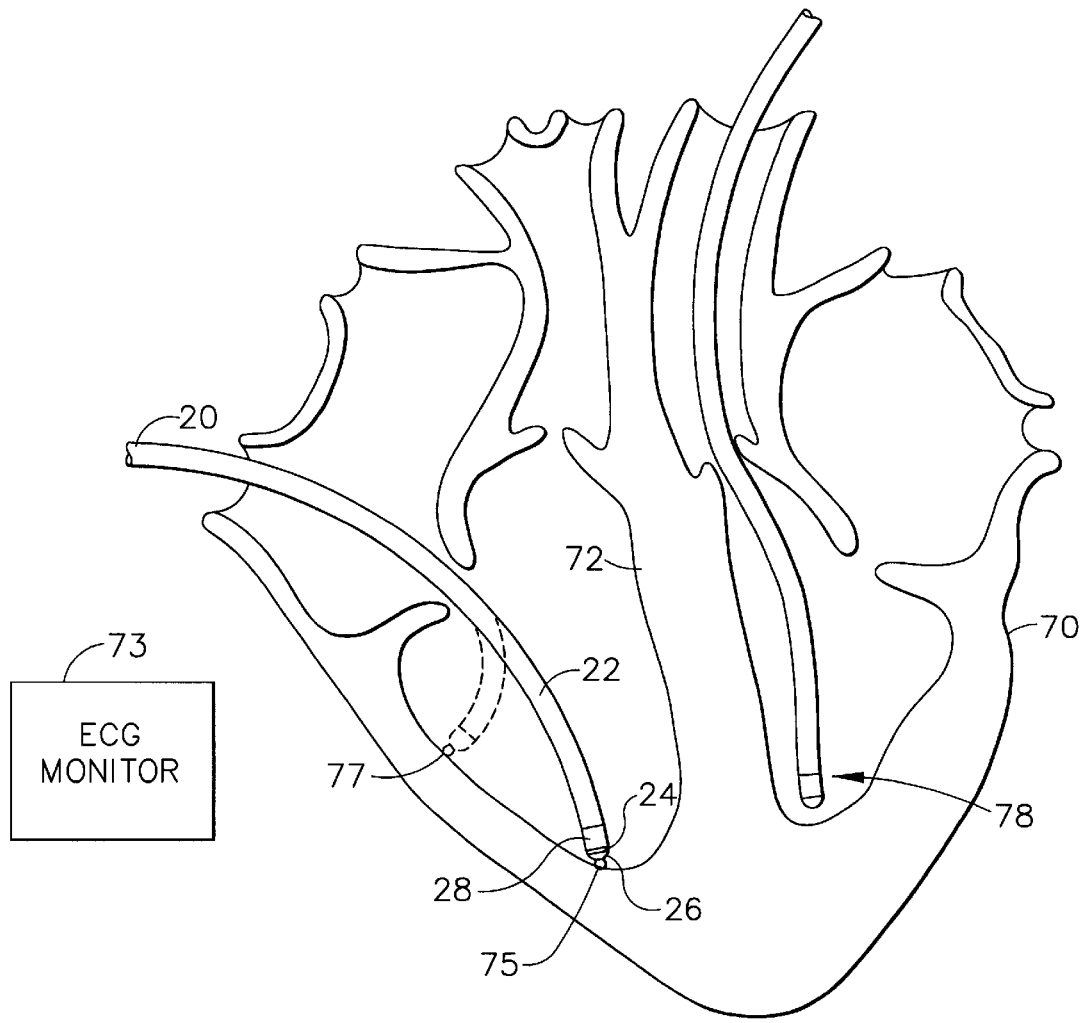
FIG. 2 shows a mapping catheter within a heart of a patient, in accordance with a preferred embodiment of the present invention.

FIG. 2 shows a distal portion of mapping catheter 20 within a heart 70 of a patient, in accordance with a preferred embodiment of the present invention. Catheter 20 is inserted into heart 70 and tip 26 is brought into contact with a plurality of locations, such as locations 75 and 77 on an inner surface 72 of heart 70. Surface 72 bounds the volume to be reconstructed, and it is locations on this surface which are to be sampled. At each of the plurality of locations, the coordinates of tip 26 are determined by device 28, preferably together with physiological information determined by functional portion 24. The determined coordinates and, optionally, physiological information form a local data point. The local data points from a plurality of locations are used for producing a map of heart 70, or of a portion of the heart.

At least one reference catheter 78 is preferably inserted into heart 70 and is placed in a fixed position relative to the heart. By comparing the positions of catheters 20 and 78, the position of tip 26 is accurately determined relative to the heart, irrespective of heart motion. Alternatively, any other suitable method may be used to compensate for movement of heart 70.

Preferably, the coordinates of tip 26 at the plurality of locations are determined at a common time-point in the cardiac cycle, preferably at end-diastole. Alternatively or additionally, each determined position is recorded together with a time-point, preferably relative to a predetermined time-point in the cardiac cycle, and together with indication of the current heart rate. The relative time-point and the rate of the cycle are used to correct for the movement of the heart. Thus, it is possible to determine positions of a large number of points, simply, in a limited time period.

Further alternatively or additionally, the position of tip 26 is determined at each location at two or more time-points in the cardiac cycle, such that for each location, a range of positions are determined. Thus, a geometric map of the plurality of locations may comprise a plurality of "snap-shots" of heart 70, each snapshot associated with a different phase of the cardiac cycle. The cardiac cycle is preferably determined using ECG monitor 73, according to physiological readings from functional portion 24, or according to movements of reference catheter 78. Preferably, each position is determined together with the heart rate at the time of determination. A frequency and phase shift transformation is preferably applied to the plurality of positions at each location to bring the positions to a state as if they were determined at common time-points with respect to a common predetermined heart rate.

Preferably, the transformation applied to the positions also serves to reduce or eliminate the effects of any movement of the heart that is not due to the cardiac cycle, particularly chest movement due to respiration or other movements of the patient. These effects are removed by defining a cyclic trajectory of the points associated with each location, and then filtering out of the trajectory frequencies of motion other than frequencies associated with the heart rate. Preferably, any frequencies whose corresponding wavelengths do not evenly divide the cardiac cycle length, as determined from the ECG, are filtered out. The result for each location is a modified trajectory, including a corrected end-diastolic point, which is then used in reconstructing the map of the heart, as described hereinbelow.

Preferably, at each location at which tip 26 is positioned, it is verified that catheter 20 is in contact with the surface, using any suitable method, for example, as described in PCT publication WO97/24981, which is incorporated herein by reference.

Figure 3:
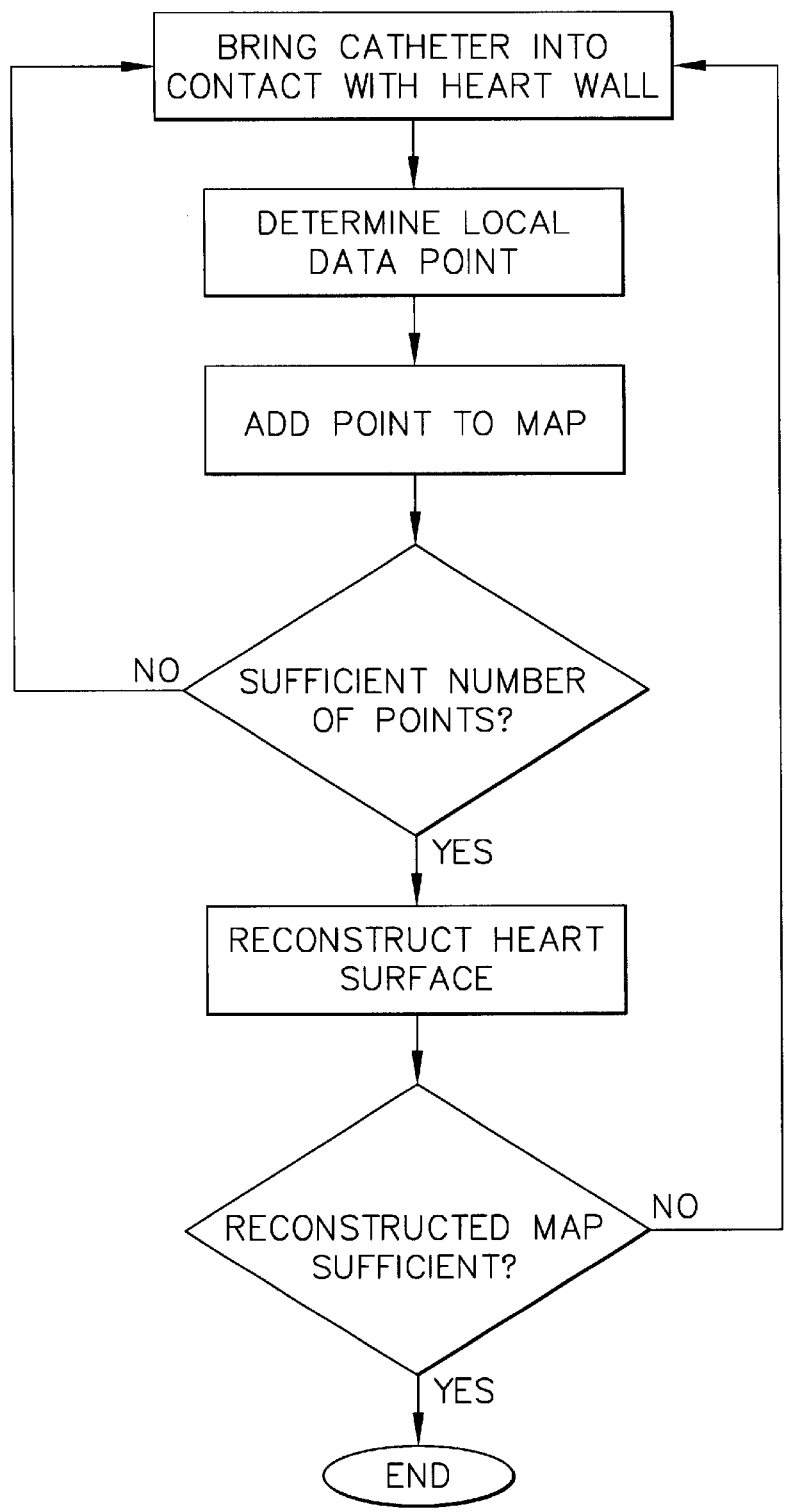
FIG. 3 is a flow chart illustrating a method of point sampling and map reconstruction, in accordance with a preferred embodiment of the present invention.

FIG. 3 is a flow chart illustrating the process of point sampling and reconstruction of a map, in accordance with a preferred embodiment of the present invention. As described above, catheter 20 is brought into contact with surface 72 of heart 70, and signals are received from the catheter to form a local data point characteristic of the location of tip 26. The local data point preferably includes coordinates of the point at a plurality of time points and one or more values, associated with the point, of at least one physiological parameter. Preferably, as mentioned above, the local data point includes an indication of the heart rate and time point in the heart cycle for each determined coordinate. The parameter values may be associated with specific time points or may be associated generally with the point.

Preferably, the contact between tip 26 and surface 72 is verified and the point is added to the map only if there is sufficient contact between the tip and the surface. In a preferred embodiment of the present invention, points for which proper contact does not exist are added to a database of interior points. These points are interior to the reconstructed surface and indicate areas on the map which are not part of the reconstructed surface. Alternatively or additionally, the user may indicate sampled points which are not to be used as part of the reconstructed surface, for example because they are outstandingly outside of the area of the other sampled points. Tip 26 is then moved to an additional location on surface 72 and data are likewise determined regarding the additional point. This procedure is repeated for a plurality of sampled points until data are determined for a sufficient number of points to make the map, or for a predetermined amount of time. Preferably, computer 36 counts the number of sampled points and compares the number of points to a predetermined required minimum number of points. Preferably, the predetermined number of points is between about ten to twenty points for fast procedures and is up to 100 points for longer procedures. Alternatively or additionally, the physician notifies computer 36 when a sufficient number of points have been sampled.

A map of heart 70 or of a volume within the heart is reconstructed, as described below, and the physician decides whether the map includes sufficient detail and appears to be accurate. If the map is not sufficient, more points are acquired and the map is accordingly updated or is again reconstructed. The reconstructed map is thereafter used for analysis of the functioning of heart 70, and the physician may decide on a required treatment accordingly.

Figure 4:
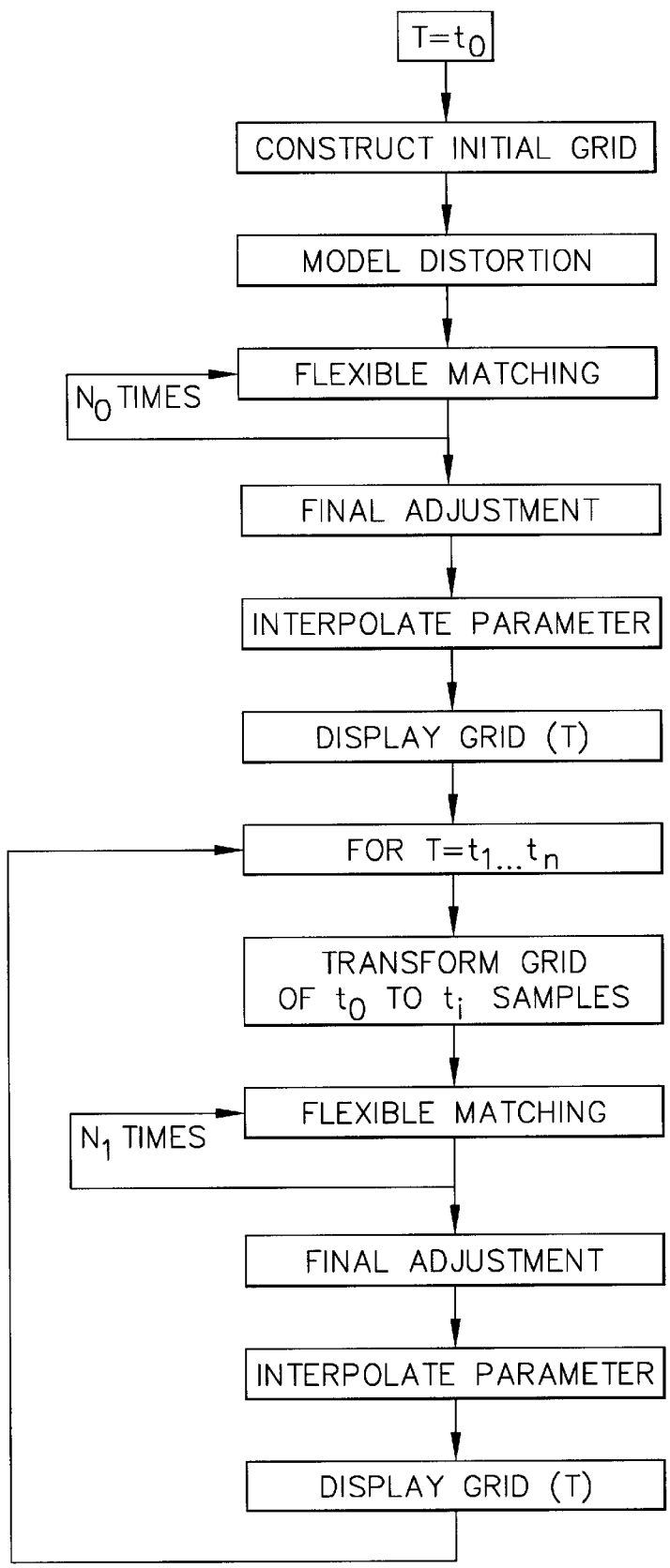
FIG. 4 is a flow chart illustrating a reconstruction procedure, in accordance with a preferred embodiment of the present invention.

FIG. 4 is a flow chart illustrating a reconstruction procedure, in accordance with a preferred embodiment of the present invention. Reconstruction is initially performed for positions determined at an anchor time point ($t_0$) of the heart cycle, such as end diastole. In a first stage of the initial reconstruction, a grid enclosing the sampled points is constructed. Thereafter, a stage of model distortion is applied to the grid, in which the grid is roughly adjusted to the shape defined by the sampled points. Subsequently, a preferably iterative stage of flexible matching is carried out finely adjusting the grid points according to the coordinates of the sampled points. Final adjustment is preferably applied to the grid including smoothing, an affine transformation and/or an exact matching stage which brings the grid to include substantially all the sampled points. The parameter values associated with the sampled points are preferably interpolated to all the grid points and the grid is subsequently displayed. This procedure is described in greater detail hereinbelow with reference to the figures that follow.

FIGS. 5A–5E are simplified, two-dimensional graphs illustrating the reconstruction procedure for a single timepoint, in accordance with a preferred embodiment of the present invention. For clarity of illustration, the figures and the following description refer to a simplified, two dimensional example. The extension of the principles illustrated herein to 3D reconstruction will be clear to those skilled in the art. Points $S_i$ are sampled points on the surface of the volume to be reconstructed, whose coordinates were received during the above-described sampling process.

Figure 5A:
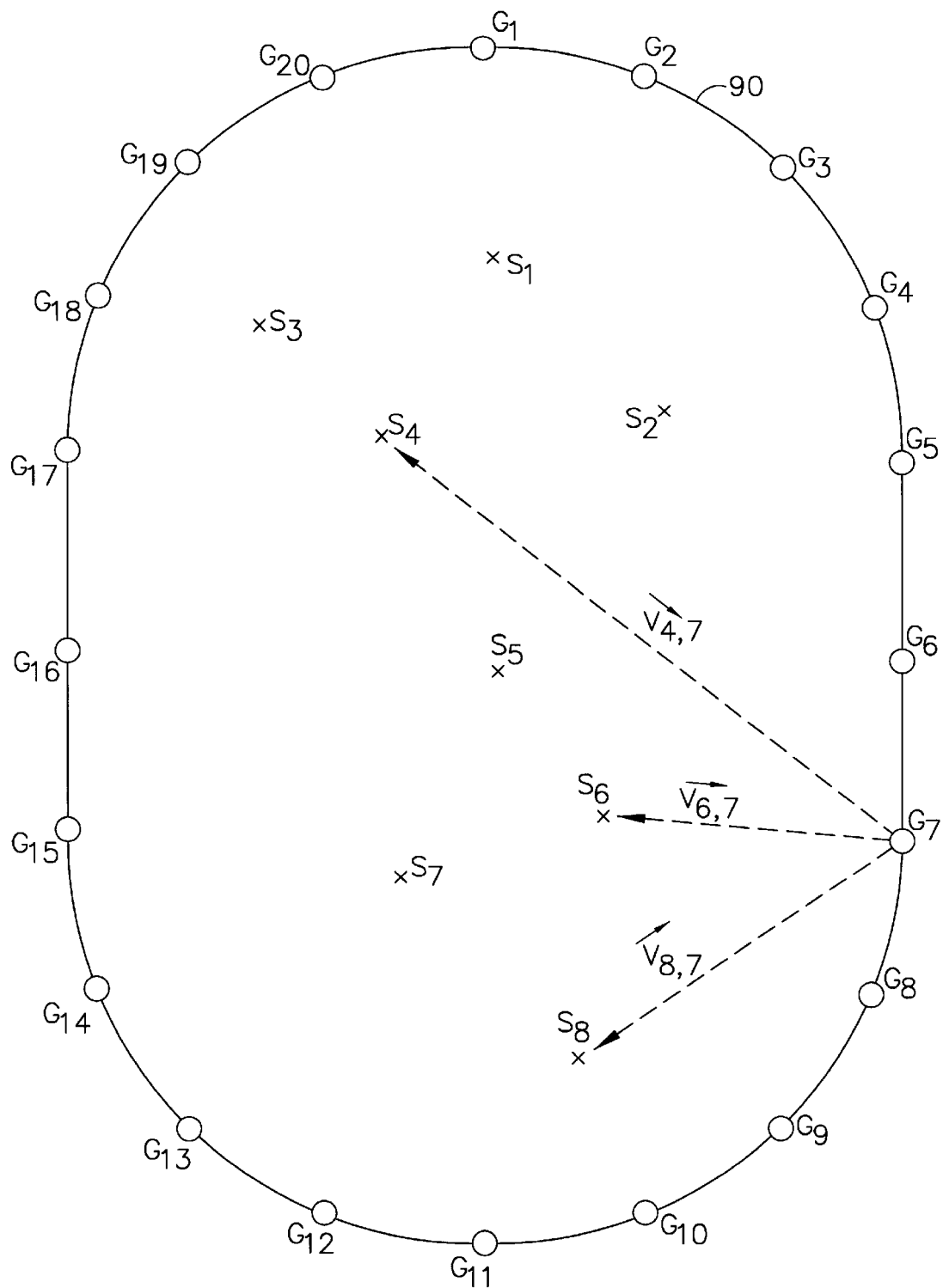
FIGS. 5A–5E are simplified, two dimensional graphs illustrating reconstruction of a map from sampled points, in accordance with a preferred embodiment of the present invention.

As shown in FIG. 5A, in the first stage, an initial grid 90 is defined in a vicinity of the sampled points, preferably enclosing the sampled points. Alternatively, grid 90 may be interior to the sampled points or pass between the points. Preferably, grid 90 comprises a number of points substantially greater than the number of sampled points. The density of the points is preferably sufficient to produce a map of sufficient accuracy for any required medical procedure. In a preferred embodiment of the present invention, the physician can adjust the density of points on the grid according to a desired compromise between reconstruction speed and accuracy. Preferably, grid 90 has an ellipsoidal shape or any other simple closed shape.

Alternatively or additionally, grid 90 has a shape based on known characteristics of the volume on whose surface the sampled points are located, for example, a shape determined by processing an LV-gram or other fluoroscopic or ultrasound image of the heart. In a preferred embodiment of the present invention, computer 36 contains a data-base of initial grids according to commonly-sampled volumes. The physician indicates, preferably via keyboard 38, which volume is being sampled and initial grid 90 is chosen accordingly. The chosen grid may be initially aligned with the sample points using any method known in the art, for example as described in Paul J. Besl and Neil D. McKay, "A method for registration of 3-D shapes," IEEE Transactions on Pattern Analysis and Machine Intelligence, 14(2) :239–258, February 1992, which is incorporated herein by reference. The initial grid may alternatively be chosen from the grid library using geometric hashing or alignment, as described, for example, in Haim J. Wolfson, "Model-based object recognition by geometric hashing," in: O. Faugeras, ed., Computer Vision-ECCV90 (First European Conference on Computer Vision, Antibes, France, Apr. 23–27, 1990), Springer, Berlin, 1990, 526–536, or in P. Huttenlocher and S. Ullman, "Recognizing solid objects by alignment with an image," International Journal of Computer Vision, 5: 195–212, 1990, which are incorporated herein by reference. After the initial alignment, the method of the present invention proceeds, preferably as shown in FIG. 4 and described further hereinbelow.

Figure 5B:
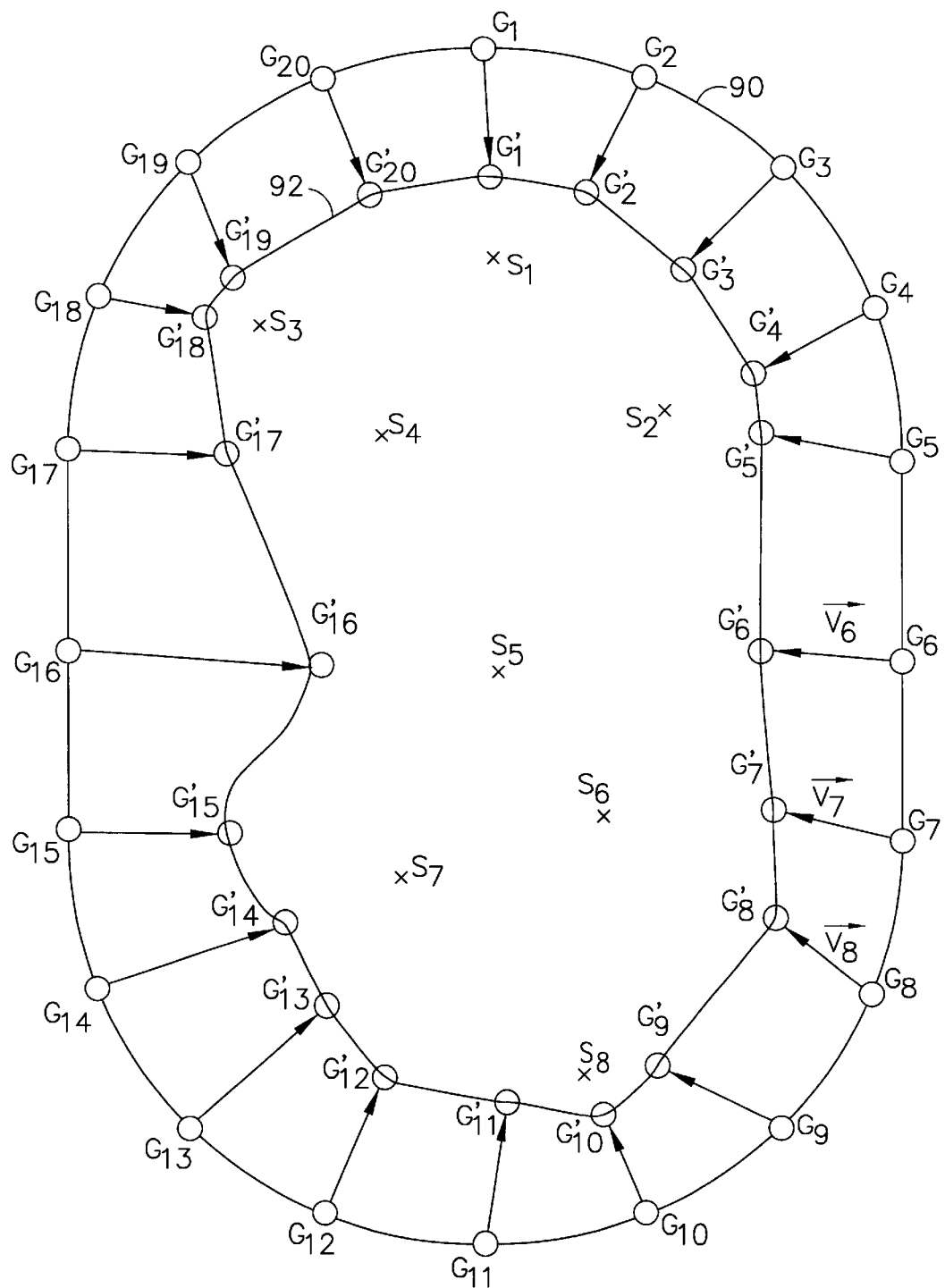

As shown in FIG. 5B, grid 90 is transformed to a grid 92 of points G', which is a rough adjustment toward the structure of the sampled volume. For each point Gj on grid 90, an adjustment vector $\vec{V}_j$ is constructed, and point Gj is replaced by a corresponding point Gj' on grid 92, which is displaced by $\vec{V}_j$ from point Gj on grid 90. Adjustment vector $\vec{V}_j$ is preferably a weighted sum of vectors $\vec{V}_{ji}$ from Gj to the sampled points $S_i$, as shown in FIG. 5A. Preferably, the weights of vectors $\vec{V}_{ji}$ in the sum are strongly inversely dependent on the magnitude of the vectors. Preferably, the weights are inversely dependent on the magnitude raised to a power (k), wherein k preferably ranges between 4 and 10, and is most preferably either between 6 and 8. In a preferred embodiment of the present invention, adjustment vectors $\vec{V}_j$ are calculated according to equation (1):

$$\vec{V}_j = C_f \sum_i \frac{\vec{V}_{ij}}{r_j^k + \varepsilon} \div \sum_i \frac{1}{r_j^k + \varepsilon}, r_j = |\vec{V}_{ij}| \quad (1)$$

In equation (1), epsilon is a small scalar, preferably, smaller than the magnitude of the smallest vector which is not zero, and is preferably of the size of the accuracy of the determination of the sampled points, for example, about $10^{-6}$. Epsilon is used to prevent division by zero when the grid point is on a sampled point, and therefore the magnitude of the vector is zero. Cf is a constant factor between 0.1 and 1, preferably between 0.5 and 0.9 most preferably about 0.75, which is adjusted to determine how closely the points $G_j'$ will approach points $S_i$ in the rough adjustment.

In a preferred embodiment, the influence of a sampled point Si on grid point Gj, takes into account not only the distance between the sampled point Si and Gj, as shown above in equation (1) but also the density of sampled points S in the vicinity of Si. Hence, the weighting factor applied to each sampled point, $$\frac{1}{r_j^k + \varepsilon},$$

is multiplied by a density value $\delta_i$, which preferably takes on values between 0 and 1. Preferably, $\delta_i$ is as defined in equation (2):

$$\delta_i = \frac{1}{\sum_j \frac{1}{(\|S_j - S_i\|^2 + 1)}} \quad (2)$$

The more points there are in the vicinity of S, the smaller value $\delta$ takes on and the less influence each point has. Preferably, the sum of influences of a plurality of points in a close vicinity is the same as the influence of a single isolated point, which preferably has a density value $\delta$ of about 1.

Figure 5C:
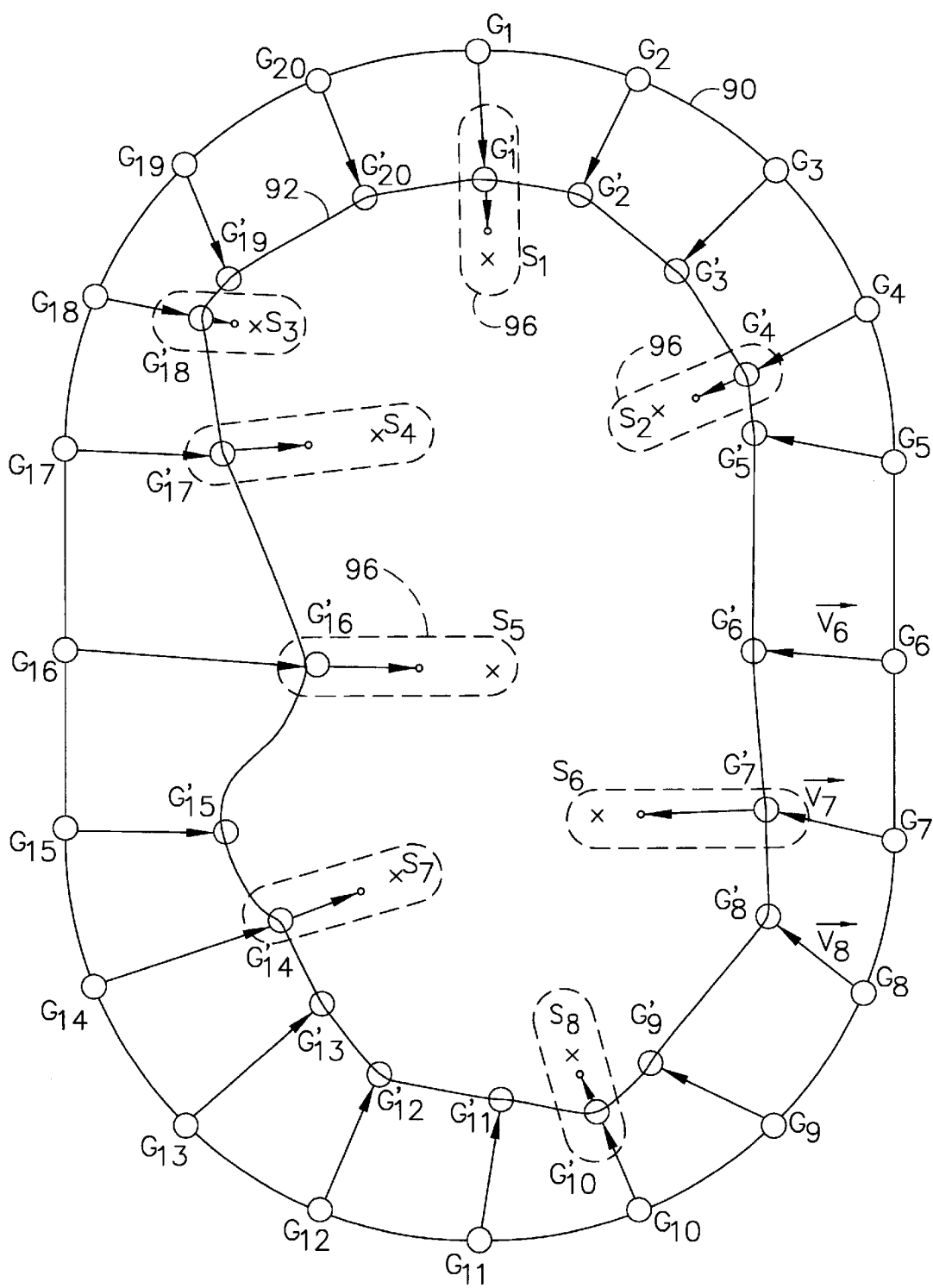

FIG. 5C illustrates a first part of a flexible matching step, in which each of sampled points $S_i$ is associated with a grid point Gj from roughly adjusted grid 92. The associated grid points are moved toward their respective sampled points, while the rest of the G' points on the roughly adjusted grid are moved according to interpolation of the movements of neighboring points on grid 92, as described further hereinbelow. Preferably, each sampled point $S_i$ is associated with the closest grid point. For example, the closest grid point to $S_1$ is $G_1'$, and these points are therefore associated. Preferably, computer 36 creates a memory list in which these pairs of points are listed. For clarity of this explanation, the associated points are marked by dashed ovals 96 in FIG. 5C.

Preferably, a transformation function f, which moves the associated grid points toward their respective sampled points, is generated. The non-associated grid points are also moved according to function f. Function f is preferably easily calculated, and transforms the grid to a smooth form. Preferably, function f is a weighted sum of the distances between the associated pairs of sampled and grid points, such that pairs of associated points close to the grid point influence its displacement more than pairs of associated points far from the grid point. Function f is preferably as given in equation (3) below, with $w_i(Gj)$ dependent on the distances between the grid point Gj and the associated grid points Gi, preferably as defined in equation (4). Alternatively, $w_i(Gj)$ is dependent on the distance between the grid point Gj and the sampled points Si, as in equation (1). In the flexible matching stage, k is preferably smaller than the power law in the rough adjustment stage in order to generate a smoother grid surface. Preferably, k in the flexible matching stage is between 2 and 6 and is most preferably 4. Preferably, k is an even number in order to simplify the calculations. Although the equations below are stated for convenience in scalar notation, it will be understood that $S_i$, $G_i$ and $f(Gj)$ are vector quantities, as in equation (1) above:

$$\vec{f}(G_j) = \frac{\sum_i w_i(G_j) \cdot (S_i - G_i)}{\sum w_i(Gj)} \quad (3)$$

$$w_i(G_j) = \frac{1}{\|G_j - S_i\|^k + C} \quad C > 0 \quad (4)$$

The constant C determines how close the associated grid points are moved toward their associated sampled points. For very small values of C, the associated grid points $G_i$ are moved substantially onto the sampled points $S_i$. Preferably, C is between 0.3 and 0.7, more preferably about 0.5. Alternatively or additionally, C is changed according to the number of times the flexible matching is to be performed. Further alternatively or additionally, in the first flexible matching step, C is relatively large, while in subsequent flexible matching steps C is gradually reduced.

The distance definition used in equations (2), (3) and (4) is preferably the Euclidean distance in $R^3$, due to its simplicity in calculation and the fact that it causes points on opposite walls of the reconstructed volume to repel one another.

In an alternative preferred embodiment of the present invention, the grid points which have an associated sampled point are moved toward their associated sampled points by a portion of the distance between them. Preferably, the points are moved a percentage of the distance between the associated pair. For example, in FIG. 5C the points are moved about ⅔ of the distance. Alternatively, the grid points are moved by any other amount dependent on the distance between the associated pair.

Figure 5D:
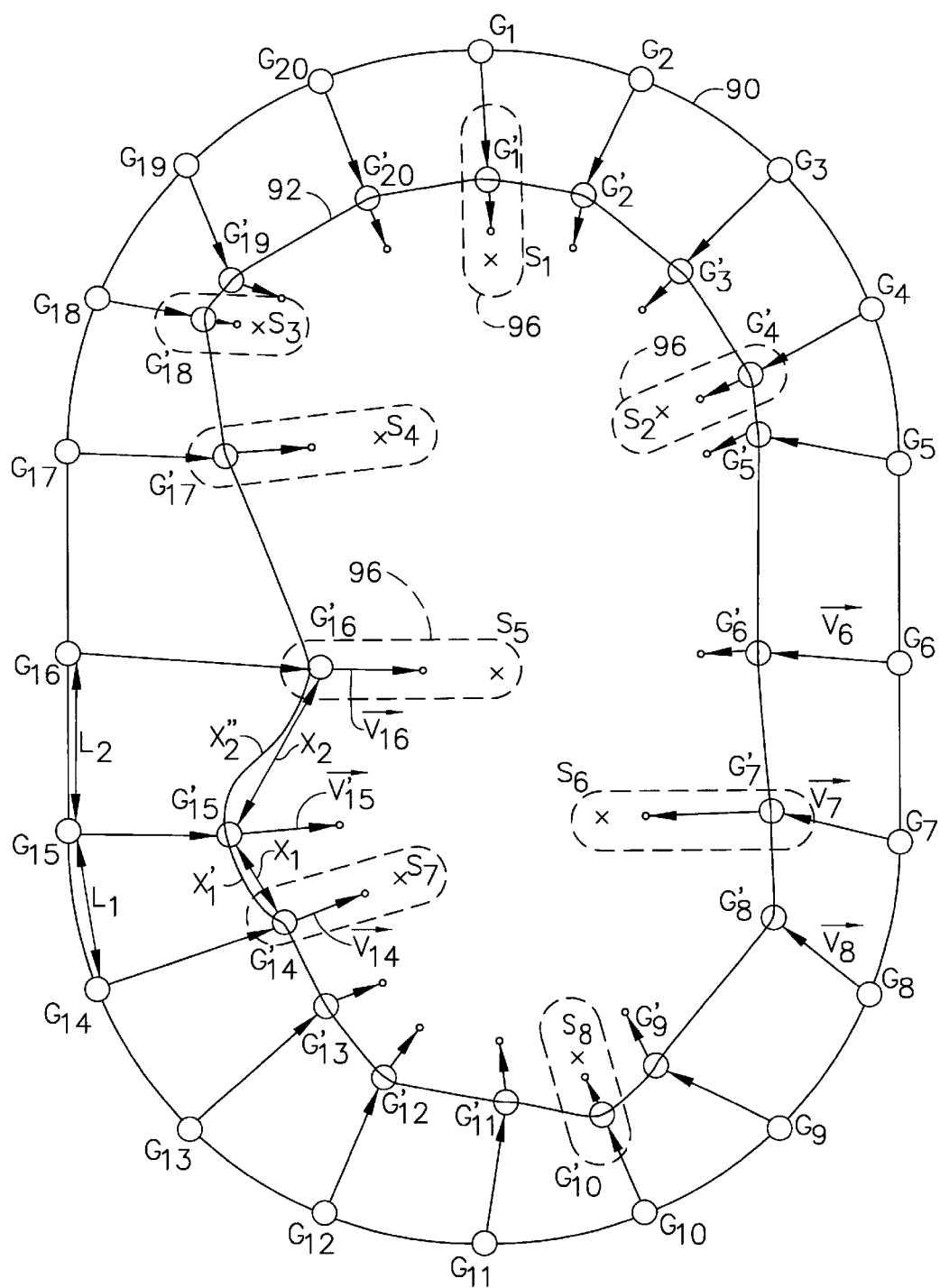

As shown in FIG. 5D, those grid points G'k which are not associated with sampled points $S_i$ are then moved according to a movement vector $\vec{V}'_k$ which is dependent on the movements of the grid points $G'_1$ surrounding the point. Preferably, the non-associated points $G'_k$ are moved a distance which is a linear interpolation of the movements of the surrounding points $G'_1$. Preferably, the distance between the grid points is determined as the geometrical distance between the points as they are on the present adjusted grid. For example, the geometrical distance between $G'_{15}$ and $G'_{16}$ is indicated by $X_2$, and may be calculated according to the coordinates of the two points. Alternatively or additionally, the distance used is the grid-distance $\tilde{X}_2$ along the present adjusted grid, the grid-distance $\tilde{L}_2$ along the original grid, or the geometrical distance $L_2$ on the original grid. In a preferred embodiment of the present invention, in a first flexible matching step, the distance used is the grid-distance—either $l_2$ or $\tilde{X}_2$—while in subsequent flexible matching steps the distance used is the geometrical distance $X_2$.

For example, as shown in FIG. 5D, point $G'_{15}$ is moved a distance defined by a vector, which is a weighted sum of vectors $\vec{V}_{14}$, and $\vec{V}_{16}$ of grid points $G'_{14}$, and $G'_{16}$, respectively. Preferably, $\vec{V}_{15}$ is as described in equation (2) below, in which $d_1$ is a selected type of distance between $G_{15}$ and $G_{14}$, and may include $X_1$, $\tilde{X}_1$, $l_1$ or any other suitable distance definition. Likewise, $d_2$ is a selected type of distance between $G_{15}$ and $G_{16}$ and may include $X_2$, $\tilde{X}_2$, $l_2$, or any other distance definition. Preferably, in the first flexible matching step illustrated in FIG. 5D, $d_1$ and $d_2$ are taken as $X_1$ and $X_2$ respectively.

$$\vec{V}'_{15} = \frac{d_2}{d_1 + d_2} \vec{V}'_{14} + \frac{d_1}{d_1 + d_2} \vec{V}'_{16} \quad (5)$$

Although equation (8) illustrates a first-order linear interpolation, it will be understood that higher-order and non-linear interpolation methods may also be used.

Preferably, during the flexible matching stage, flexible matching steps are repeated a few times ($N_0$ times, as shown in FIG. 4). Each time, grid points are associated with the sampled points, and the associated and non-associated grid points are moved accordingly.

The rough adjustment and flexible matching tend to cause the grid to become non-uniform. Therefore, during a final adjustment stage the grid is preferably smoothed, for example, by applying a surface convolution with a Gaussian-like kernel. Preferably, the kernel is a 3×3 Gaussian kernel, and is applied to the grid a plurality of times, preferably between five and ten times. Alternatively, a larger kernel may be used in which case it may be applied to the grid fewer times, most preferably only once. The surface convolution, however, generally causes shrinkage of the surface, and therefore a simple transformation, preferably an affine transformation, is applied to the grid to cancel the shrinkage and improve the matching of the grid to the sampled points. The affine transformation is preferably chosen as the transformation which minimizes the mean square distance between sampled points outside of the grid and a surface defined by the grid. This choice of the transformation causes substantially all the sampled points to be on or inside the surface defined by the grid. This choice is in accordance with the anatomical structure of the heart in which outliers, i.e., points not on the sampled surface, are generally inside the sampled surface, i.e. inside a cardiac chamber rather than on the myocardial wall. Thus, the reconstructed grid is properly reconstructed by ignoring outliers which otherwise may deform the grid incorrectly.

To conclude the final adjustment stage, the user may optionally request an exact matching stage in which the grid surface is deformed to include substantially all the sampled points. Preferably, for each sampled point not on the grid surface as a result of prior stages, a closest grid point is chosen and moved to the position of the sampled point. The rest of the grid points are preferably not moved. Preferably, internal points which are beyond a certain distance from the grid surface are not moved in this stage and are regarded as outliers. It is noted that external points are not generally distanced from the grid surface due to the affine transformation described above.

Figure 5E:
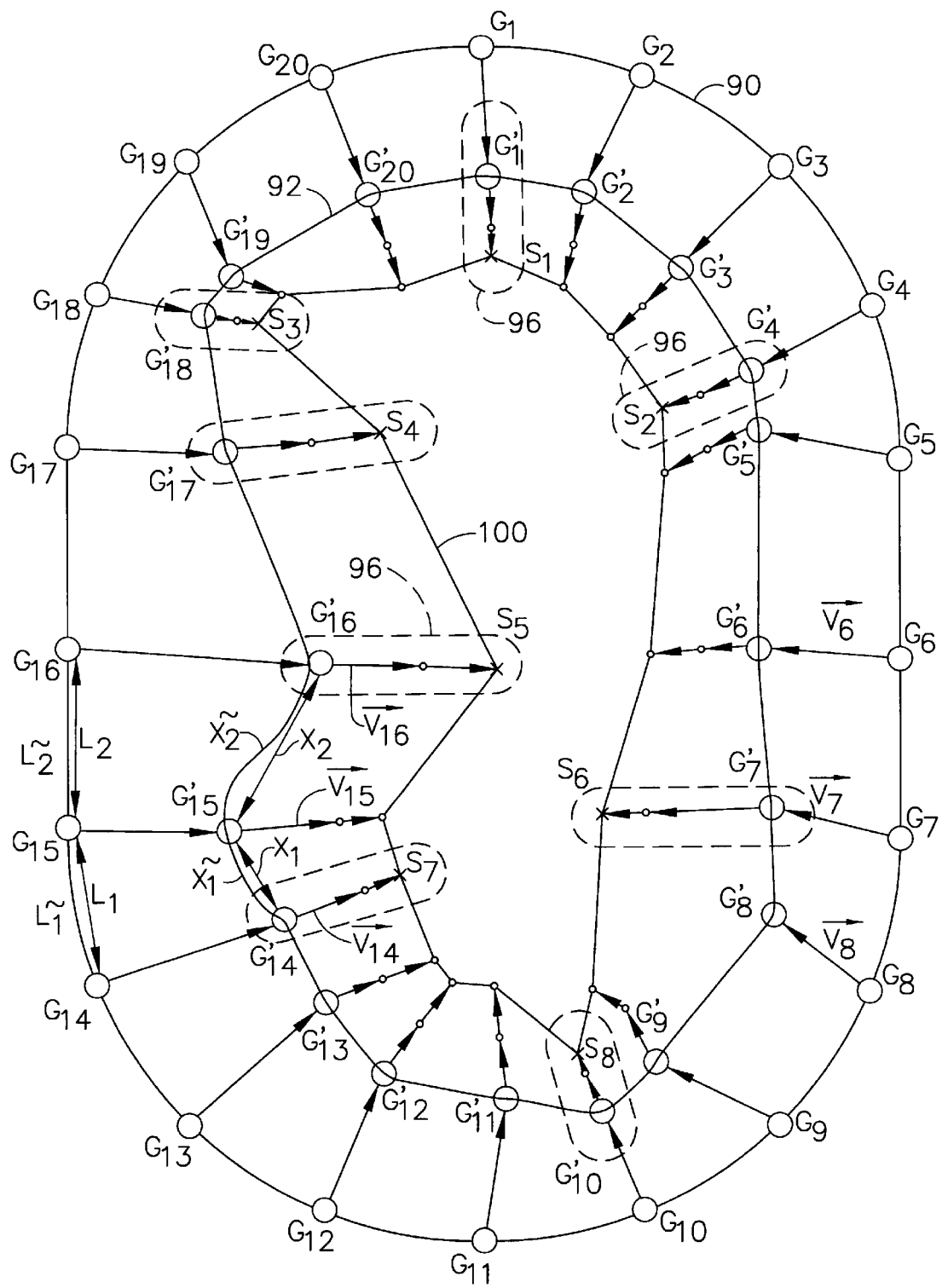

Alternatively or additionally, a last flexible matching step is performed in which the associated grid points are moved onto the sampled points, as shown in FIG. 5E. Curved line 100 in FIG. 5E represents the final grid configuration and comprises an accurate approximation of the sampled volume.

Alternatively, the flexible matching is performed in one step, and the associated points from the rough adjustment grid are immediately moved onto the sampled points. In a preferred embodiment of the present invention, computer 36 first produces an approximate map, in which the flexible matching is performed in one step. The approximate map is used by the physician to decide if more sampled points are needed. Once the physician decides that no more points are needed, computer 36 reconstructs a more accurate map in which the flexible matching is performed a plurality of times. Meanwhile, the physician may use the approximate map in order to save time. In further preferred embodiments, the first reconstructed map is produced with a relatively low density of points on the grid, while later reconstructions use a more dense grid.

Referring back to FIG. 4, when the sampled points include data from more than one time point, the reconstructed grid of the anchor time point (hereinafter referred to as the anchor grid) is preferably used to quickly reconstruct the grid for the other time points $t_i$. For each of the other time points, a simple transformation is performed on the anchor grid to bring the grid close to the form of the sampled points of time $t_i$. The simple transformation is preferably a quadratic transformation or an affine transformation. Alternatively, the transformation comprises a rotation and/or scaling transformation. In some preferred embodiments of the present invention, the transformation is chosen according to the number of sampled points. Preferably, when there are a relatively large number of sampled points, a quadratic transformation is applied, while for fewer sampled points, simpler transformations are employed.

Flexible matching is then preferably performed on the transformed grid one or more times ($N_T$), preferably fewer times than were required in reconstruction of the anchor-time grid ($N_T<N_0$), most preferably twice. Final adjustments are then preferably applied to the grid, and the resulting grid at time $t_i$ may be displayed. The parameter value may also be interpolated separately for time $t_i$, substantially as described above with respect to the anchor grid. When reconstruction for all of the time points is concluded, the reconstructed grids may be displayed in sequence as a function of time, or in any other manner. Preferably, the reconstruction process continues while the anchor grid is displayed, so that a physician may use the reconstructed data without delay.

Preferably, as noted hereinabove, each data point includes at least one physiological parameter, such as an indicator of the electrical activity in the heart, measured using functional portion 24 of catheter 20. After the map is constructed, as described above, the points on the grid, $G_1$, $G'_4$, $G'_7$, etc., that were associated with sampled points $S_1$, $S_2$, $S_6$, etc., are assigned the physiological parameter value of their respective sampled points. The non-associated grid points receive parameter values by interpolation between the values of the parameters of neighboring associated grid points in a manner similar to that described above. Alternatively or additionally, the non-associated grid points receive parameter values in a manner similar to the way they received their coordinates in flexible matching.

Further alternatively or additionally, the non-associated grid points are given parameter values using a zero-order-hold filling in method. Starting from the sampled points, all the surrounding grid points are given the same parameter value as the sampled point has, propagating outward until another grid point with a different parameter value is encountered. Thereafter, a Gaussian smoothing process is preferably applied to the parameter values. Thus, parameter values are given in a very simple method to all the grid points substantially without forfeiting visual clarity.

Thus, a 3D map is reconstructed showing both the geometrical shape of the heart chamber and local electrical parameters or other physiological parameters as a function of position in the heart. The local parameters may include electrogram amplitude, activation time, direction and/or amplitude of the electrical conduction vector, or other parameters, and may be displayed using pseudocolor or other means of graphic realization, as is known in the art. Preferably, a predefined color scale is associated with the parameter, setting a first color, e.g., blue, for high values of the parameter, and a second color, e.g., red, for low values of the parameter.

Figure 6:
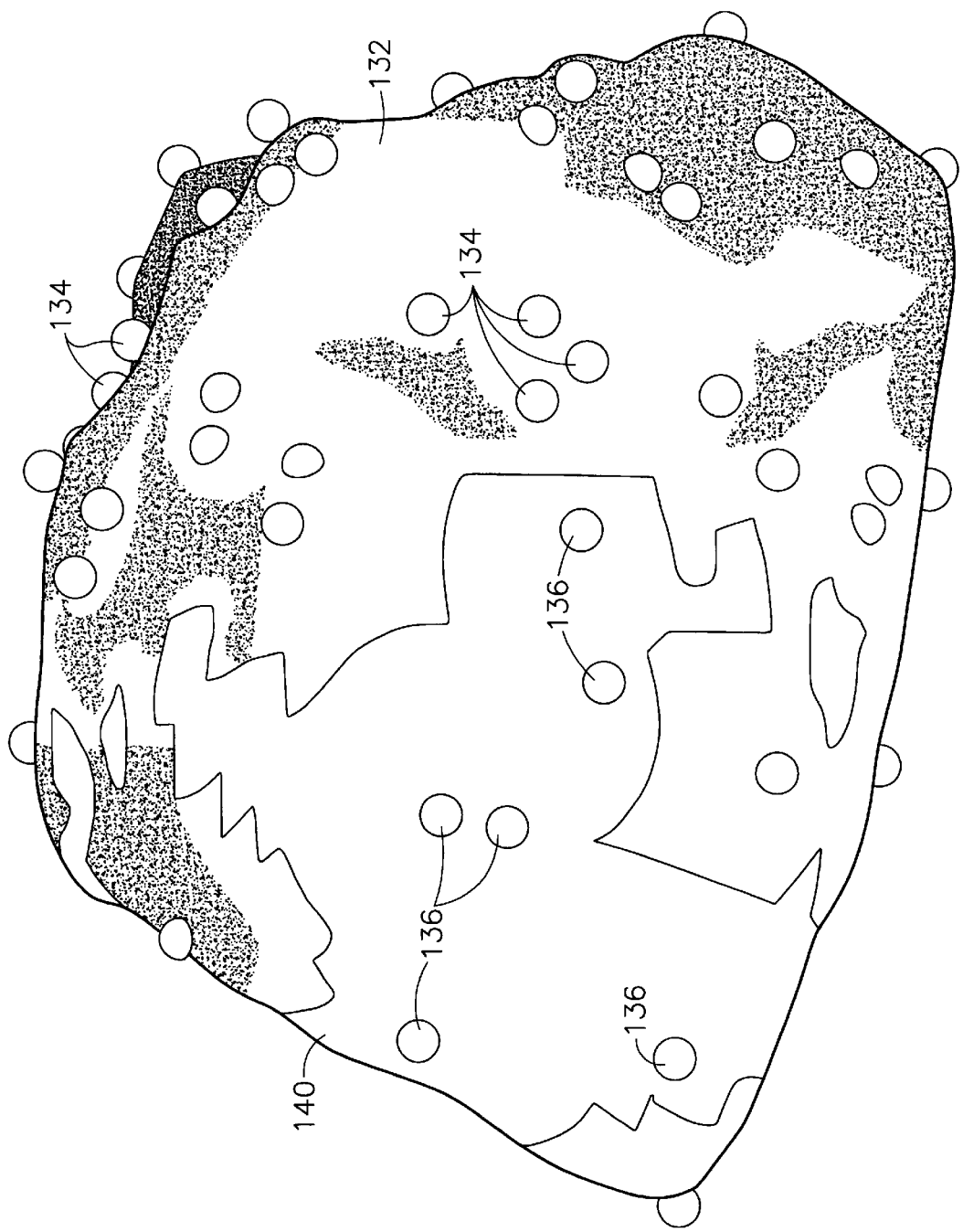
FIG. 6 is a schematic illustration of a displayed reconstructed heart volume, in accordance with a preferred embodiment of the present invention.

FIG. 6 is a schematic illustration of a displayed reconstructed heart volume 130, in accordance with a preferred embodiment of the present invention. A plurality of sampled points 134 are used to reconstruct a surface 132 of volume 130. A grid (not shown) is adjusted as described above to form surface 132. Preferably, each point on the grid receives a reliability value indicative of the accuracy of the determination. Further preferably, the reliability value is a function of the distance from the grid point to the closest sampled point on surface 132 and/or of a density of sampled points 134 in a vicinity of the grid point. Preferably, areas of surface 132 covered by less-reliable grid points, such as an area 140, are displayed as semi-transparent, preferably using α-blending. Due to the transparency, points 136 on an inner surface of volume 130 are displayed, being seen through volume 130. Preferably, the user may define the predetermined distance and/or sample density defining less-reliable points. Alternatively or additionally, different levels of semi-transparency are used together with a multi-level reliability scale.

Figure 7:
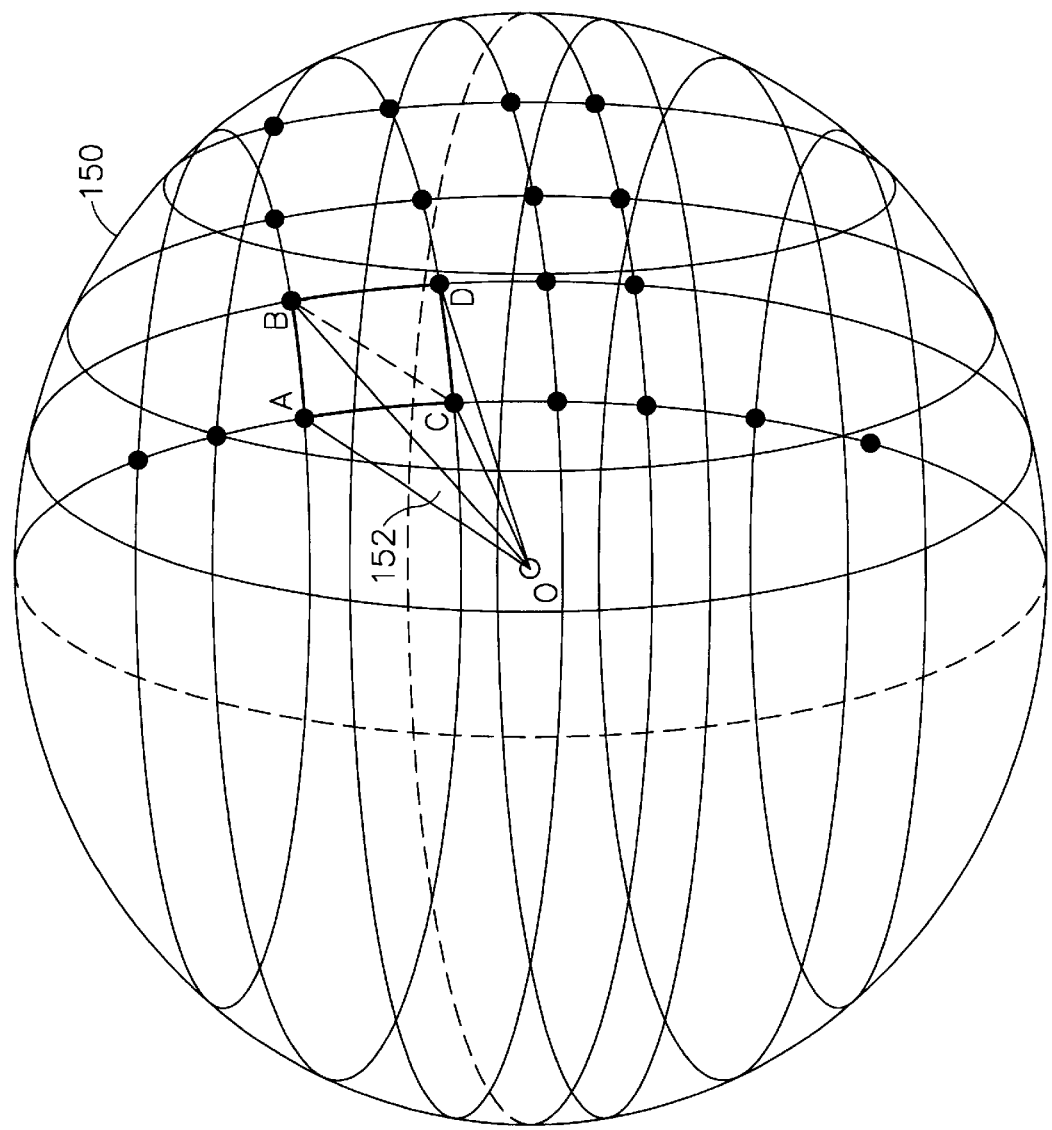
FIG. 7 is an illustration of a volume estimation method, in accordance with another preferred embodiment of the present invention.

FIG. 7 is a schematic illustration of a volume estimation method, in accordance with a preferred embodiment of the present invention. In some cases it is desired to estimate the volume encompassed by one or more reconstructed surfaces, for example, to compare the volume of a heart chamber at different time-points of the heart cycle. In FIG. 7 the reconstructed grid surface is represented, for clarity, by a ball 150. The surface of ball 150 is partitioned into quadrilaterals by the grid points, and these quadrilaterals are used for volume estimation. An arbitrary point O, in a vicinity of the surface, preferably within the volume, most preferably close to the center of mass of ball 150, is chosen, thus defining a pyramid 152 for each quadrilateral on the surface of ball 150. An estimate of the sum of the volumes of pyramids 152 accurately represents the volume of ball 150.

Preferably, each quadrilateral is divided into two triangles, and the volume is estimated by summing the volumes of tetrahedrons defined by these triangles as bases and vertex O apex. Let $A_m$, $B_m$, $C_m$, denote the vertices of the m-th triangle arranged clockwise, so that the normals of the triangles point outward from the surface of ball 150. The volume V of ball 150 is estimated by equation (6):

$$V = \frac{1}{6}\sum_m (B_m - A_m) \times (C_m - A_m) \cdot (O - A_m) \qquad (6)$$

Figure 8:
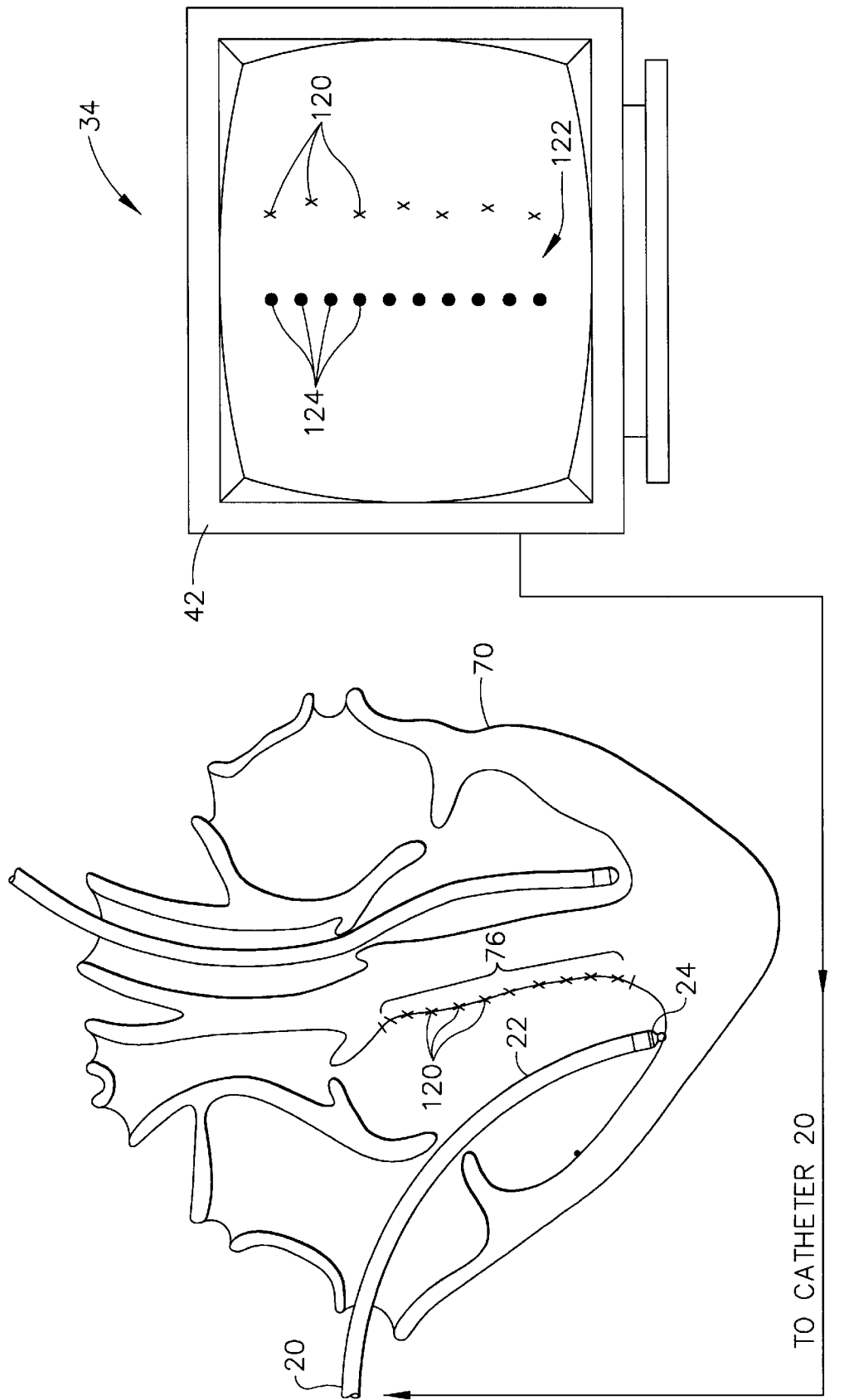
FIG. 8 is an illustration of a reconstruction procedure, in accordance with another preferred embodiment of the present invention.

FIG. 8 is an illustration of a reconstruction procedure, in accordance with another preferred embodiment of the present invention. In this preferred embodiment the sampled points are known to be on a single, open surface, rather surrounding a 3D volume, and therefore the beginning grid may comprise an open plane, rather than a closed curve. Catheter 20 is brought into contact with a plurality of locations on an inner wall 76 of heart 70, and the coordinates of these locations are determined to give sampled points 120. Preferably, a physician indicates to console 34 the direction from which catheter 20 contacts surface 76. Computer 36 accordingly generates an initial grid 122, which includes a plurality of grid points 124, such that all the grid points are preferably on one side of the sampled points. The adjustment procedure is performed substantially as described above, bringing grid points 124 to maximally resemble surface 76.

In a preferred embodiment of the present invention, the adjustment procedure may be performed step-by-step on display 42, allowing the physician to interrupt and direct the procedure if necessary.

It is noted that although the above description assumes that the data regarding the sampled points are acquired by the system which performs the reconstruction, the reconstruction procedure may also be performed on points received from any source, such as from a different computer, a library database or an imaging system. Furthermore, although preferred embodiments are described herein with reference to mapping of the heart, it will be appreciated that the principles and methods of the present invention may similarly be applied to 3D reconstruction of other physiological structure and cavities, as well as in non-medical areas of 3D image reconstruction.

As noted above, an important example of a physiological parameter of the heart, that is measured using functional portion 24 of catheter 20 and that is assigned to the grid points that are associated with the sampled points, is the local activation time (LAT) of the heart tissue. This time is determined by referring the time of a feature of the signal (specifically, a voltage) measured by functional portion 24 at each sampled point, for example, the time in the cardiac cycle at which that signal first exceeds a certain threshold, to the time within the cardiac cycle of a fiducial feature of the ECG signal, as measured, for example, using ECG monitor 73. Preferably, the grid on which LAT is posted is the grid corresponding to end diastole, because the heart is most fully expanded at that point in the cardiac cycle, and the interior surfaces of the chamber of the heart consequently are smoothest at that point in the cardiac cycle.

The values of LAT, that are posted at the grid points associated with the sampled points, are interpolated to the other grid points, as described above. Preferably, this interpolation is done using a variant of the zero-order-hold filling method, based on the distance d(V) from each grid point V to the nearest sampled points, as measured along the grid.

Initially, the grid points that coincide with sample points are assigned d(V) values of zero, and all the other grid points are assigned d(V) values of infinity. Then, in each of a sequence of iterations, each grid point V is visited in turn, and is assigned a new value of d(V), based on the distance d(V,$N_i$) between that grid point V and its m neighboring grid points $N_i \in \{N_i, \ldots, N_m\}$. Specifically, d(V) is replaced with min[d(V),$\min_i$(d($N_i$)+d(V,$N_i$))]. As each grid point V is assigned a new value of d(V), that grid point V also is assigned the LAT value associated with the neighbor $N_i$ upon which the new value of d(V) is based. These iterations are continued as long as at least one d(V) changes in the course of an iteration. Finally, the posted LAT values are smoothed by convolution, as described above in the context of the final adjustment of grid geometry.

Figure 9:
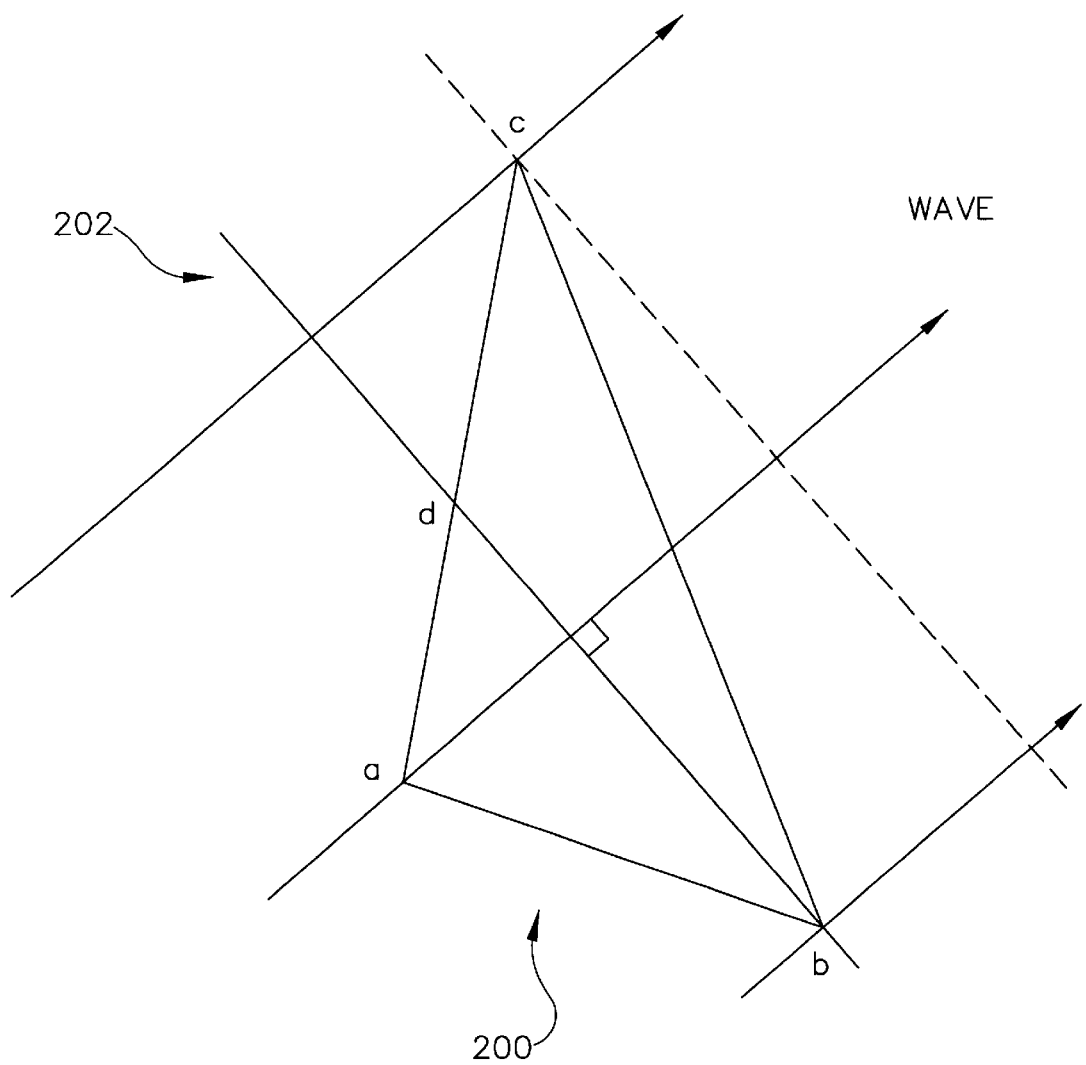
FIG. 9 shows a planar wavefront crossing a grid triangle.

The preferred 3D grid is one in which the grid points are connected by lines in a way that defines the grid as a collection of polygons, for instance triangles, with the grid points constituting the vertices of the triangles and with the lines connecting the grid points constituting the edges of the triangles. In such a grid, a preliminary version of the propagation velocity of the activation signal, i.e., the conduction velocity of the heart tissue, is obtained by assigning a velocity vector to each triangle, based on the LAT values at the triangle's vertices. It is assumed that the grid is sufficiently fine that, in each triangle, the activation signal propagates as a plane wave. FIG. 9 shows a triangle 200 with vertices $\vec{a}$, $\vec{b}$ and $\vec{c}$, and with a planar wavefront 202 propagating across triangle 200 towards the upper right at a velocity $\vec{v}$. Note that wavefront 202 is perpendicular to the direction of propagation. Wavefront 202 is shown at the time $t_b$ at which wavefront 202 reaches vertex $\vec{b}$. This time is at least as great as the time $t_a$ at which wavefront 202 reached vertex $\vec{a}$, and is no greater than the time $t_c$, at which wavefront 202 will reach vertex $\vec{c}$: $t_a \leq t_b \leq t_c$. Wavefront 202 intersects side ac of triangle 200 that is opposite vertex $\vec{b}$ at a point $\vec{d}$. Point $\vec{d}$ is found by linear interpolation:

$$\vec{d} = \frac{t_b - t_a}{t_c - t_a}\vec{c} + \frac{t_c - t_b}{t_c - t_a}\vec{a} \qquad (7)$$

The unit vector in the direction of $\vec{v}$ is found by taking the cross product of $\vec{d} - \vec{b}$ with the unit vector $\vec{N}$ normal to triangle 200 and normalizing:

$$\frac{\vec{v}}{\|\vec{v}\|} = \frac{\vec{d} - \vec{b}}{\|\vec{d} - \vec{b}\|} \times \vec{N} \qquad (8)$$

Finally, the magnitude of $\vec{v}$ is found by projecting the apparent velocity from $\vec{a}$ to $\vec{c}$ onto this unit vector:

$$\|\vec{v}\| = \frac{\vec{c} - \vec{a}}{t_c - t_a} \cdot \frac{\vec{v}}{\|\vec{v}\|} \qquad (9)$$

Having thus assigned a velocity vector to each triangle of the grid, each grid point is assigned a raw velocity vector by averaging the velocities of all the triangles of which that grid point is a vertex. Finally, the raw velocities are smoothed iteratively, as follows:

1. Each triangle is assigned, as a new velocity, the average of the velocities assigned to the grid points which are the vertices of the triangle.

2. Each grid point is assigned, as a new velocity, the average of the velocities assigned to the triangles of which the grid point is a vertex.

Preferably, the conduction velocity vector function thus obtained is displayed superposed on a display of the surface represented by the grid, both as a pseudocolor map, as described above, or as arrows emerging from the grid points. In one variant of this display, the direction of the arrow at each grid point corresponds to the direction of $\vec{v}$ as posted and smoothed at that grid point; and the length of the arrow corresponds to the magnitude of $\vec{v}$ as posted and smoothed at that grid point. Alternatively, all the arrows have the same length, and the arrows are displayed in monochrome or achromatic manner, using a gray scale that encodes the magnitudes of $\vec{v}$. Alternatively, the arrows may be displayed according to a specific color scheme. The iterative smoothing parameters may be determined by a priori knowledge of the specific heart.

It will be appreciated that any vector function that is derived from a set of scalar measurements on the surface of a biological structure may be displayed in this manner. Furthermore, the vector function may be displayed along with the scalar measurements from which it was derived, or along with a scalar function of the scalar measurements from which the vector function was derived. For example, LAT may be displayed as a pseudocolor map, and the corresponding conduction velocity vector function may be displayed as arrows superposed on the pseudocolor map, as described above.

Figure 10:
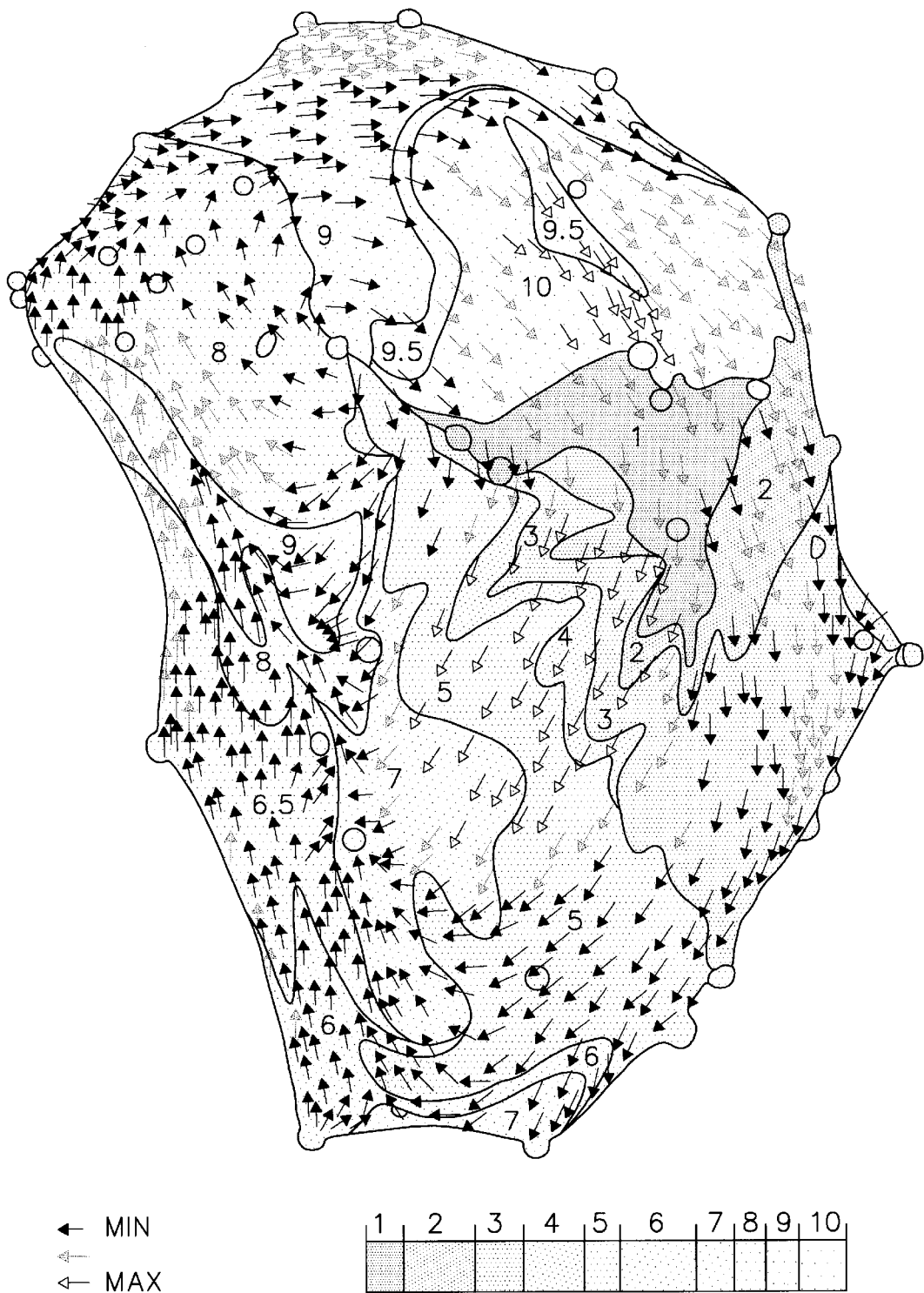
FIG. 10 shows a combined LAT—conduction velocity display for a normal human atrium.

FIG. 10 shows such a display of a normal human atrium. LAT is normally displayed as a scale in pseudocolor, but is herein depicted with a numerical scale. The numerical scale with respect to the LAT ranges from a minimum (1) which is the earliest activation time, to a maximum (10) which is the latest activation time. The direction of the corresponding conduction velocity vector field is shown by the arrows. The arrows are displayed in monochrome, with the gray scale level of each arrow corresponding to the magnitude of the associated conduction velocity vector. As is shown in the lower left hand portion of the figure, the velocity magnitude scale ranges from a minimum (solid black arrow) to a maximum (open headed arrow). Midrange is shown with a dotted arrow. The signal flow is predominantly radially away from the region numbered one (1) in which activation is initiated.

Figure 11:
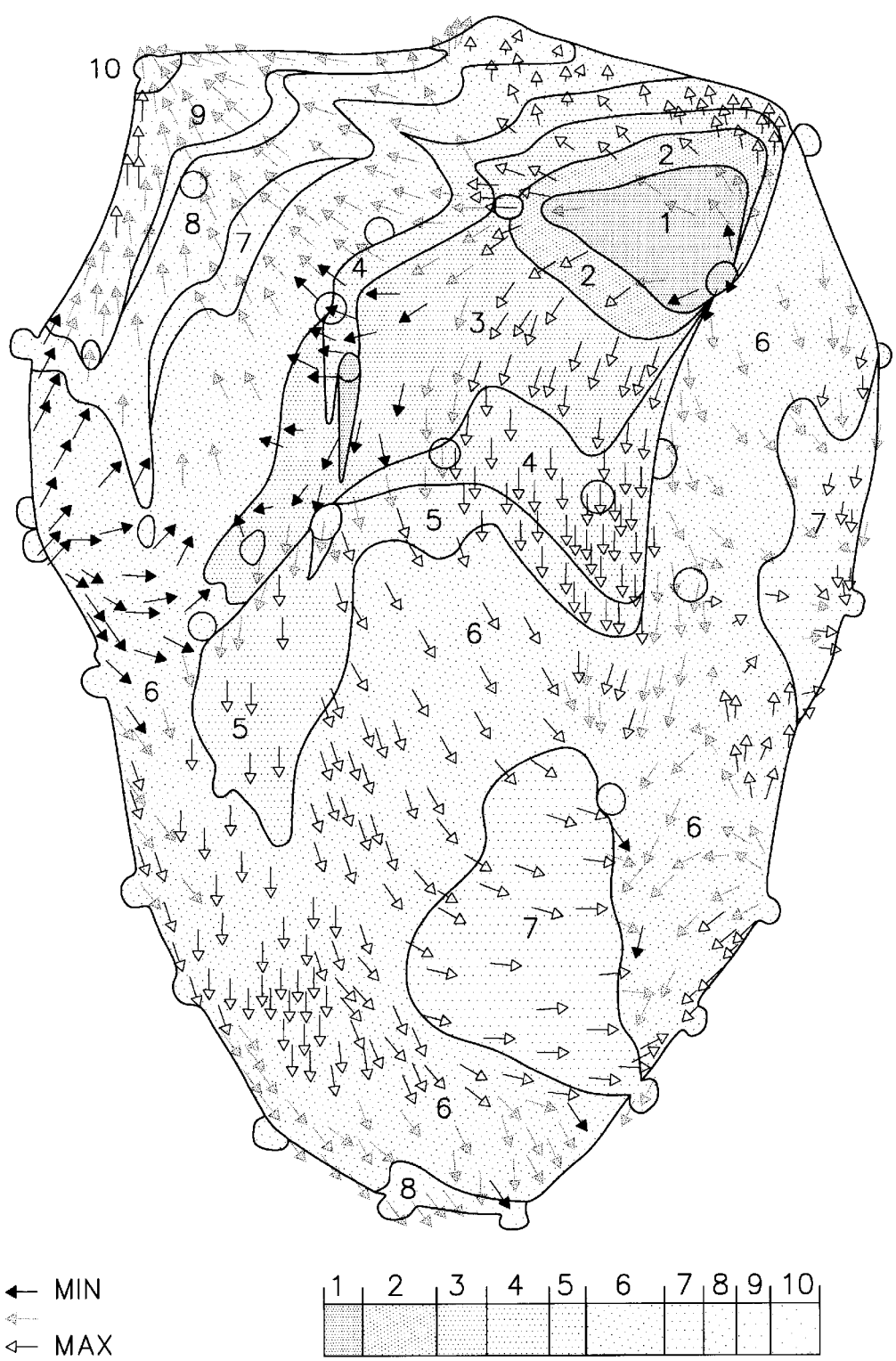
FIG. 11 shows a combined LAT—conduction velocity display for a human atrium suffering from atrial flutter.

FIG. 11 is a similar display of LAT and conduction velocity in a human atrium suffering from atrial flutter. The signal flow tends to be vortical, rather than radially outward. This vortical flow is evidenced by the distinct and separate patterns of conduction velocity vector arrows shown.

Figure 12:
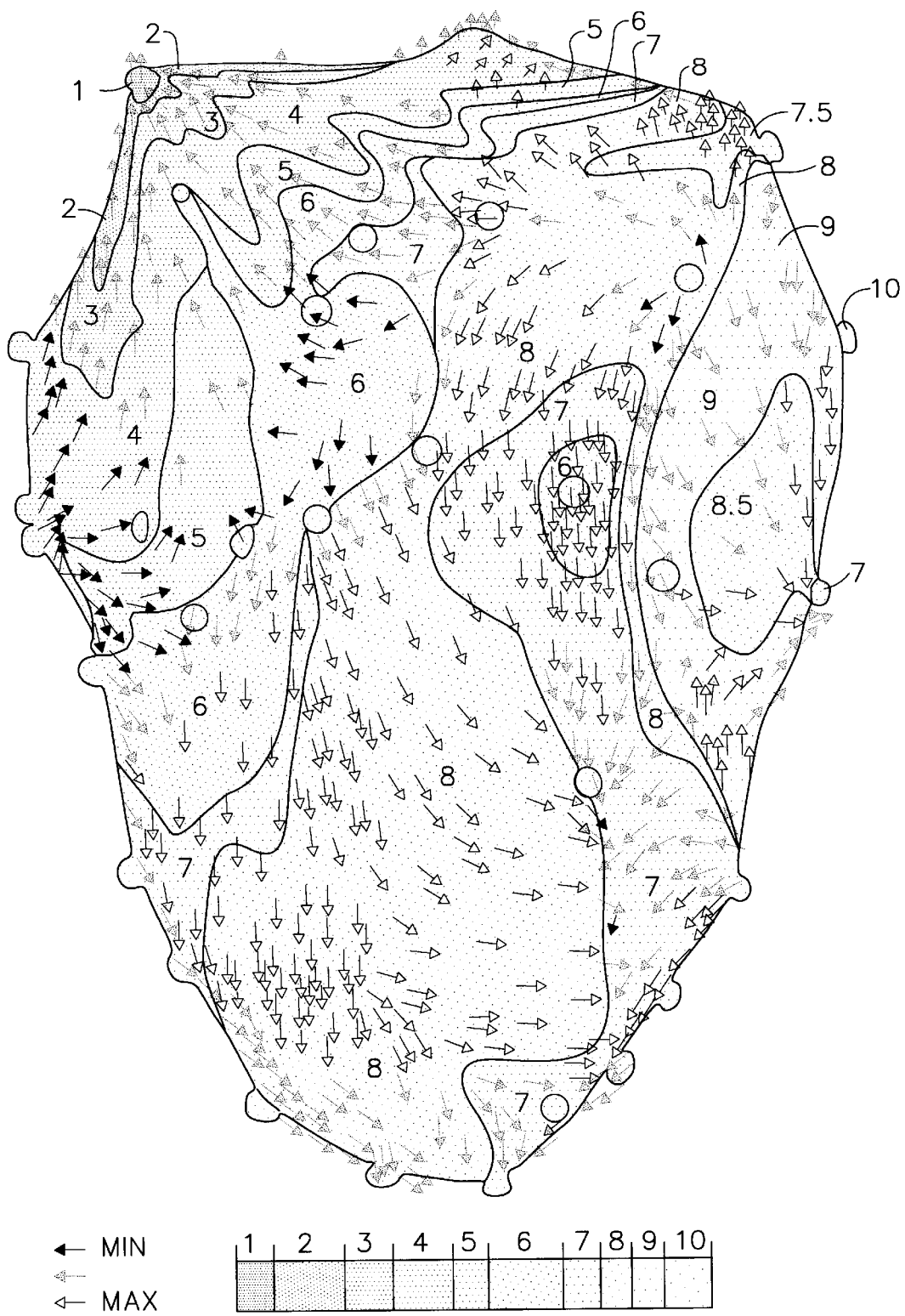
FIG. 12 shows a pattern, on a combined voltage range—conduction velocity plot, that is diagnostic of ventricular tachycardia for a human ventricle.

FIG. 12 shows a pattern on such a display that is diagnostic of ventricular tachycardia: a region of scar tissue associated with a vortical conduction velocity field that is represented by circular patterns of arrows. LAT is shown with a numerical scale from 1 to 10. A physician treats ventricular tachycardia thus diagnosed by ablating the heart tissue in the region of the pattern shown in FIG. 12. Such a display also provides quality control diagnostics, inasmuch as the magnitude of the conduction velocity is expected to be abnormally low in scar tissue.

Figure 13:
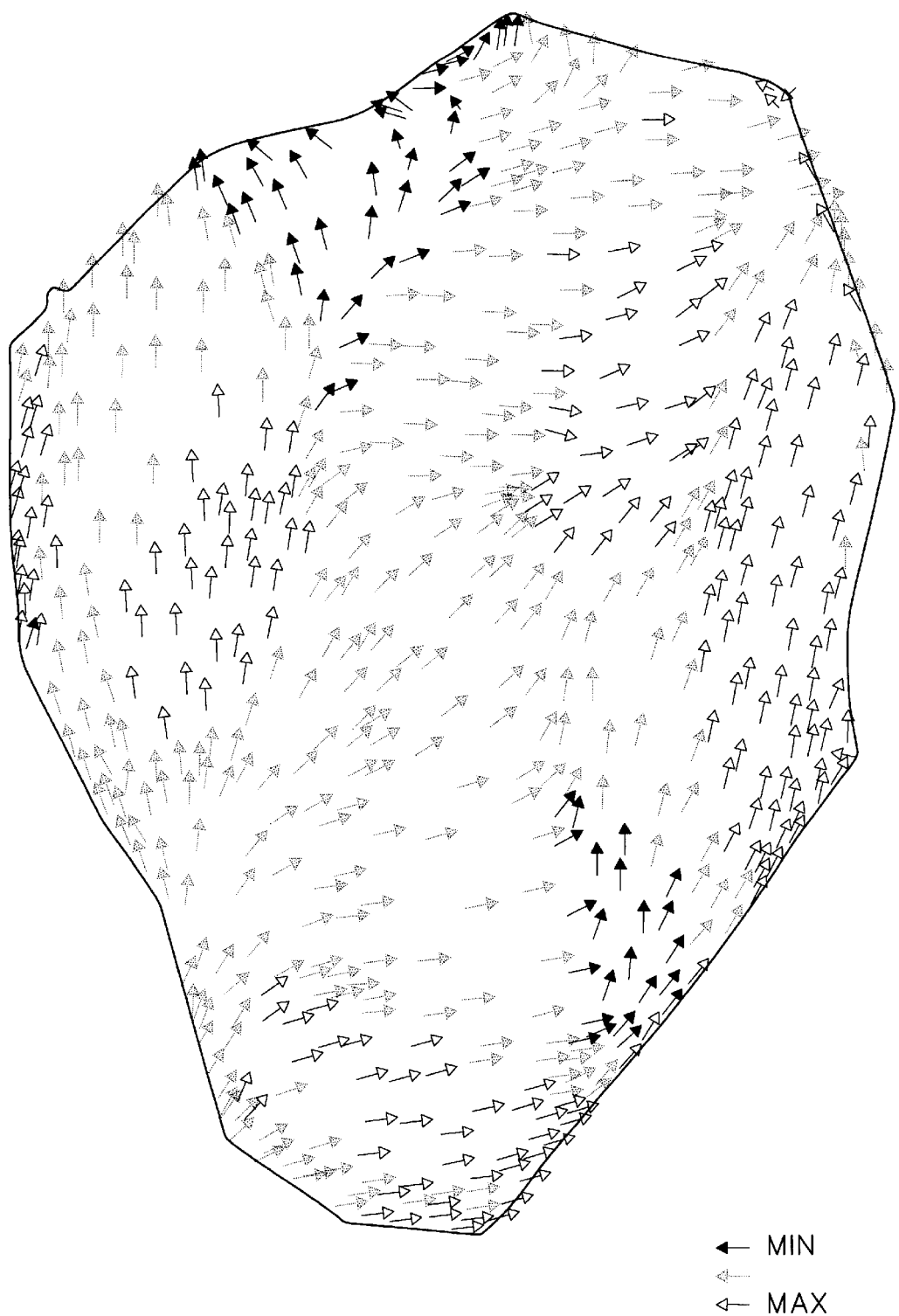
FIG. 13 shows a conduction velocity display in the left ventricle of a dog wherein the heart is entrained in a sinus rhythm from the right ventricle apex.

FIG. 13 shows the conduction velocity vectors alone (without display of LAT regions) in the left ventricle of a dog. The heart is entrained in a sinus rhythm from the right ventricle apex. The velocity vector arrows are distributed according to the density of the underlined grid. Each arrow represents the local conduction velocity. The arrow direction is the computed direction of the conduction and its gray scale color represents the conduction velocity magnitude (black colored arrows indicate slow conduction velocity, gray colored arrows indicate midrange conduction velocity and white colored arrows indicate fast conduction velocity).

Figure 14:
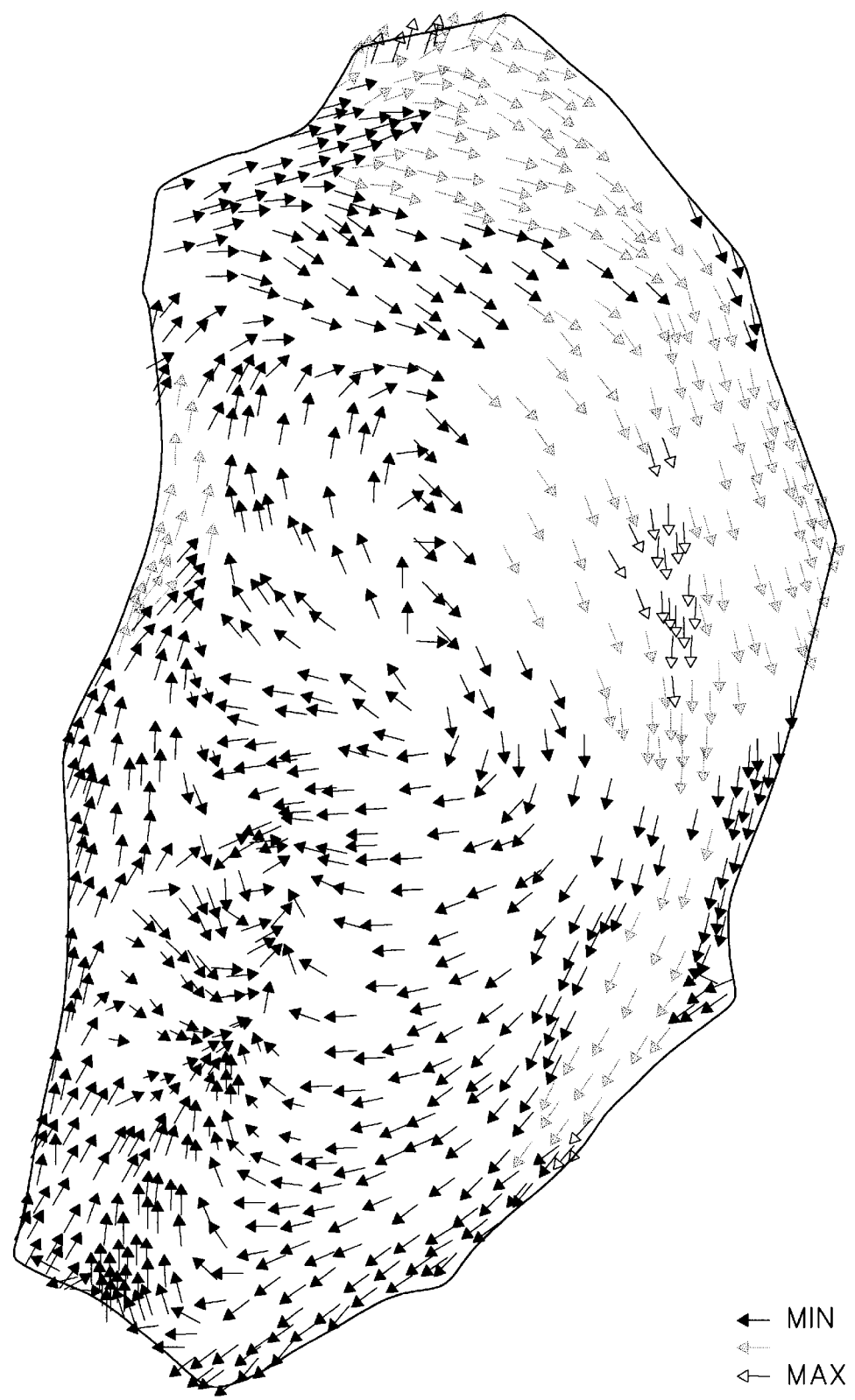
FIG. 14 shows a conduction velocity display of the right atrium of a human heart suffering from atrial flutter.

FIG. 14 is the right atrium of a human heart suffering from atrial flutter. The conduction velocity vectors are also depicted alone, e.g. without display of LAT regions or other parameters. Rather than having a well-defined focus that starts the activation in the heart, such as that found in the heart example depicted in FIG. 10, the cardiac wave, as depicted by the conduction velocity vectors, moves in distinct circular patterns. These circulated patterns result in a convergence of the cardiac wave as shown along the lower central portion of the atrium. One type of treatment involves ablations along this area of the atrium in order to disable the abnormal circuitry. After ablation, the chamber can be remapped to ensure that the procedure has been performed successfully.

Other scalar functions of the ECG measurements used to derive LAT also are useful. One such scalar function is the amplitude (maximum–minimum) of voltages measured at each sampled point over the course of the cardiac cycle. A low amplitude is diagnostic of scar tissue. Most preferably, voltage amplitude, LAT and conduction velocity are displayed together. Voltage amplitude is encoded in a conventional pseudocolor map. LAT is encoded as colored dots posted on the sampled points. Conduction velocity is displayed as arrows, as described above.

As mentioned previously, once the conduction velocity vectors, (indicated by arrows), are displayed superimposed on the 3D map of the surface of the heart, treatment may be administered to those areas of the heart depicted as being problematic based on the displayed velocity vectors. For instance, ablative treatment is administered at those areas depicting velocity vector direction, e.g. converging arrows such as shown in FIGS. 11 and 14. It is within the scope of the present invention to include any type of treatment modality such as the application of energy, for example laser, therapeutic ultrasound, radiofrequency, etc. as well as pharmaceutical or biological therapy. Moreover, therapeutic treatment may be administered based on the magnitude of the velocity vectors. For instance, in the gray scale embodiment, those velocity vector arrows that are identified by the color black indicate low conduction velocity. Since the propagation wave is identified to move slowly through this portion of the heart, this may be indicative of diseased tissue or scar tissue.

Another useful quality control diagnostic is obtained by displaying yet a third scalar field. This scalar field is obtained by performing calculations of conduction velocity as described above, but excluding, from each calculation, one of the sampled points, with a different sampled point being excluded from each calculation. This is done for each sampled point, thereby producing as many calculations of the conduction velocity field as there are sampled points. The associated scalar field is, at each grid point, the range (maximum–minimum) of conduction velocity magnitudes obtained at that grid point. This scalar field, displayed in pseudocolor, provides a measure of the reliability of the calculated conduction velocity field at each grid point.

It is also possible to display the conduction velocity with other physiological maps, for example, the voltage map or the impedance map, generated for the same recordings of the organ.

It is noted that the above displays may be displayed in at least two ways: by a color from the pseudocolor scale when the value represents one that is of a determined confidence level and as such, may be placed directly on the pseudocolor map; and by another, different color or transparency, when the value is of low confidence and as such, is so displayed on the map. In the latter case, the practitioner will be guided to acquire more samples.

It will thus be appreciated that the preferred embodiments of the invention described above are cited by way of example, and the full scope of the invention is limited only by the claims which follow.

What is claimed is:

1. A method of displaying a condition in a heart, comprising the steps of:
   (a) creating a map of a surface of the heart;
   (b) measuring a physiological response at at least three sampled points on the surface of the heart;
   (c) calculating a vector function related to said response; and
   (d) displaying a representation of said vector function on said map.

2. The method of claim 1, wherein said vector function is related to a gradient of said physiological response.

3. The method of claim 2, wherein said physiological response is a function of time.

4. The method of claim 1, wherein said physiological response is a local activation time (LAT) of a physiological signal propagating in the heart.

5. The method of claim 4, wherein said vector function is a velocity of said propagation.

6. The method of claim 5, including treating an area of said heart based on said vector function.

7. The method of claim 1, including treating an area of said heart based on said vector function.

8. The method of claim 1, wherein said representation of said vector function includes an arrow at each of said sampled points.

9. The method of claim 1, including representing said surface of said heart as a grid including a number of grid points, said number of grid points being at least as great as said at least three sampled points.

10. The method of claim 9, wherein each grid point substantially coincides with a corresponding one of said at least three sampled points.

11. The method of claim 9, wherein said grid includes a plurality of polygons defined by a plurality of vertices, each vertex of each said polygon being one of said grid points, and wherein said calculating of said vector function includes the steps of:

(i) interpolating a local activation time (LAT) value at each grid point;

(ii) for each of said polygons, assigning a value of said vector function to said each polygon, based on said interpolated LAT value at said grid points that are vertices of said each polygon; and (iii) for each of said grid points, determining a value of said vector function for said each grid point, based on said values of said vector function that are assigned to said at least one polygon whereof said each grid point is a vertex.

12. The method of claim 11, wherein said calculating of said vector function further includes the step of:

(iv) smoothing said values of said vector function at said grid points.

13. The method of claim 12, wherein an extent of said smoothing is based on a priori information about the condition.

14. The method of claim 11, wherein said polygons are triangles.

15. The method of claim 11, including treating an area of said heart based on said vector function.

16. The method of claim 8, wherein said arrow indicates a direction of said vector function at each sampled point.

17. The method of claim 16, wherein said arrow has a length which indicates a magnitude of said vector function at each sampled point.

18. The method of claim 16, wherein said arrow is depicted according to a gray scale which indicates a magnitude of said vector function at each sampled point.

19. The method of claim 16, wherein said arrow is depicted according to a color scheme which indicates a magnitude of said vector function at each sampled point.

* * * * *